United States Patent
Shishikura et al.

Patent Number: 6,096,743
Date of Patent: *Aug. 1, 2000

[54] 1,2,3,4-TETRAHYDROQUINOXALINEDIONE DERIVATIVE

[75] Inventors: Jun-ichi Shishikura; Hiroshi Inami; Shuichi Sakamoto; Shin-ichi Tsukamoto; Masao Sasamata; Masamichi Okada, all of Ibaraki; Mitsuo Fujii, Chiba, all of Japan

[73] Assignee: Yamanouchi Pharmaceuticals Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/809,087
[22] PCT Filed: Sep. 25, 1995
[86] PCT No.: PCT/JP95/01922
  § 371 Date: Mar. 5, 1997
  § 102(e) Date: Mar. 5, 1997
[87] PCT Pub. No.: WO96/10023
  PCT Pub. Date: Apr. 4, 1996

[30] Foreign Application Priority Data

Sep. 27, 1994 [JP] Japan .................................. 6-231908
Mar. 17, 1995 [JP] Japan .................................. 7-059482

[51] Int. Cl.[7] ..................... A61K 31/498; C07D 403/10
[52] U.S. Cl. ........................ 514/249; 514/81; 544/337; 544/354
[58] Field of Search ............... 544/354; 514/249

[56] References Cited

U.S. PATENT DOCUMENTS 5,283,244  2/1994  Sakamoto et al. ...................... 514/249
5,654,303  8/1997  Kornberg et al. ....................... 514/249
5,750,525  5/1998  Huth et al. ............................. 514/249

FOREIGN PATENT DOCUMENTS 556393     8/1993   European Pat. Off. .
7-165756   6/1995   Japan ........................... C07D 233/64
93/08173   4/1993   WIPO .
94025469   11/1994  WIPO .................................. 544/354

OTHER PUBLICATIONS

Lubisch et al., *Chemical Abstracts*, vol. 126, No. 126493 (1997).
Lubisch et al., *Chemical Abstracts*, vol. 123, No. 256765 (1995).
Lubisch et al., *Chemical Abstracts*, vol. 125, No. 10856 (1996).

*Primary Examiner*—Emily Bernhardt
*Attorney, Agent, or Firm*—Sughrue, Mion, Zinn, Macpeak & Seas, PLLC

[57] ABSTRACT

A 1,2,3,4-tetrahydroquinoxalinedione derivative represented by the following formula (I) or salt thereof, an NMDA-glycine receptor and/or AMPA receptor antagonist or kainic acid neurotoxicity inhibitor containing the derivative or salt. In addition, a pharmaceutical composition comprising said compound and a pharmaceutically acceptable carrier:

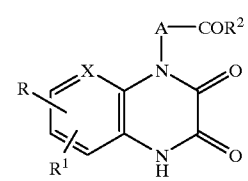

wherein the substituents are as described in the specification.

3 Claims, No Drawings

1,2,3,4-TETRAHYDROQUINOXALINEDIONE DERIVATIVE

TECHNICAL FIELD

The present invention relates to a quinoxalinedione derivative or a salt thereof which has glutamate receptor antagonizing action, has high affinity with AMPA receptors which are non-NMDA receptors, has potent inhibitory action against kainic acid neurotoxicity and audiogenic seizure inhibitory action, and has high solubility. The present invention also relates to an agent for inhibiting kainic acid neurotoxicity, which comprises the quinoxalinedione derivative or a salt thereof as an effective ingredient. The present invention further relates to a pharmaceutical composition comprising the quinoxalinedione derivative or a salt thereof and a pharmaceutically acceptable carrier.

BACKGROUND ART

Amino acids such as L-glutamic acid and L-aspartic acid are known to be central nervous system neurotransmitters. It is said that extracellular accumulation of these excitatory amino acids and their continuous of excessive stimulation of the nerves lead to Huntington chorea, Parkinson disease, epilepsy, Alzheimer disease, senile dementia or neurodegeneration or deficiency in mental and motor functions observed after the condition of cerebral ischemia, oxygen deficiency or hypoglycemia.

It has come to be considered that a regulator of the abnormal activity of an excitatory amino acid is useful for the therapeutic treatment of neurodegeneration or psychic diseases.

Excitatory amino acids exhibit their action through glutamate receptors which are specific receptors existing at postsynapse or presynapse. At present, such receptors can be classified into three groups based on electrophysiological and neurochemical studies.

1) NMDA (N-methyl-D-aspartate) receptor
2) non-NMDA receptor
   a) AMPA [2-amino-3-(3-hydroxy-5-methyl-4-isoxazolyl)propionic acid] receptor
   b) kainate receptor
3) metabotropic glutamate receptor The compound according to the present invention has glutamate receptor antagonizing action and inhibitory action against kainic acid neurotoxicity and is useful as an anti-ischemia or as an psychotropic.

L-glutamic acid or L-aspartic acid activates the above-described glutamate receptors and transmits excitation. When an excess amount of NMDA, AMPA or kainic acid is caused to act on the neuron, neuronal death occurs. It is reported that 2-amino-5-phosphonovalerianic acid or 2-amino-7-phosphonoheptanic acid which is a selective antagonist against the NMDA receptor is effective for experimental animal models suffering from neuropathy, epilepsy or cerebral ischemia (*J. Pharmacology and Experimental Therapeutics*, 250, 100 (1989); *J. Pharmacology and Experimental Therapeutics*, 240, 737 (1987); or *Science*, 226, 850 (1984)).

It is reported that NMDA receptor functions are allosterically regulated by a glycine receptor (*Eur. J. Pharmacol.*, 126, 303 (1986)), while it is reported that HA-966 which is an antagonist against the glycine receptor is effective in experimental animal models suffering from cerebral ischemia (Annual meeting of Society for Neuroscience, 1989).

It is also reported that NBQX (6-nitro-7-sulfamoylbenzo[f]quinoxaline) which is a selective antagonist against the AMPA receptor is also effective in experimental animal models suffering from cerebral ischemia (*Science*, 247, 571 (1990)).

On the other hand, it has been shown that all the non-NMDA receptors subjected to cloning have affinity with kainic acid and it is suggested that among these receptors, a receptor having low affinity with kainic acid (the AMPA/kainate receptor) has a relation with neuronal death at the time of ischemia such as cerebral infarction (P. C. May and P. M. Robison, *J. Neurochem.*, 60, 1171–1174 (1933)). This AMPA/kainate receptor has high affinity with AMPA but the binding sites of AMPA and kainic acid are not known. It is however reported that AMPA and kainic acid exhibit different electrophysiologic responses against the AMPA/kainate receptor. It is reported that in a neuronal toxicity test using a neuronal culture system, kainic acid itself causes marked neuronal cell death, while the action of AMPA alone is weak (P. C. May and P. M. Robison, *J. Neurochem.*, 60, 1171–1174 (1993)). Accordingly, there is a possibility that neuronal death caused by excessive excitation by glutamic acid at the time of ischemia is intensely suppressed by a compound having inhibitory action against kainic acid toxicity in the neuronal culture system.

There are several reports on diketoquinoxaline derivatives having an NMDA-glycine receptor antagonizing action and/or AMPA receptor antagonizing action (an unexamined published Japanese patent application (kokai) No. 63-83074, an unexamined published Japanese patent application (kokai) No. 63-258466, an unexamined published Japanese patent application (kokai) No. 1-153680, an unexamined published Japanese patent application (kokai) No. 2-48578, an unexamined published Japanese patent application (kokai) No. 2-221263, an unexamined published Japanese patent application (kokai) No. 2-221264, an international patent publication WO92/07847 and an international patent publication WO93/08173).

DISCLOSURE OF THE INVENTION

The compound according to the present invention has, as will be described hereinafter in detail, an antagonizing action against a quinoxaline-based glutamate receptor, high affinity for the AMPA receptor which is a non-NMDA receptor, intense inhibitory action against kainic acid neurotoxicity and audiogenic seizure depressant action, and also has high solubility.

The present inventors have carried out further studies on diketoquinoxaline derivatives. As a result, it was found that a compound having a —A—COR$^2$ group on the 1- or 4-position of the diketoquinoxaline skeleton has an excellent pharmacological action (inhibitory action against kainic acid neurotoxicity, anticonvulsant effect against audiogenic seizure, or the like) and also has high solubility and is therefore a compound of high utility, resulting in the completion of the present invention.

The present invention therefore provides a 1,2,3,4-tetrahydroquinoxalinedione derivative or 1,2,3,4-tetrahydropyrido[2,3-b]pyrazine derivative represented by the following formula (I):

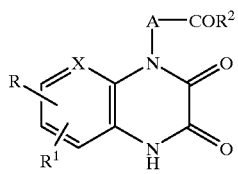

(I)

wherein symbols in the above formula represent the following meanings, respectively:

X: a nitrogen atom or a group represented by the formula CH,

R: an imidazolyl group or a di-lower alkylamino group, $R^1$: (1) a halogen atom, a nitro group, a cyano group, a carboxyl group, an amino group, a mono- or di-lower alkylamino group, a lower alkanoyl group, a lower alkylthio group, a lower alkylsulfinyl group, a lower alkylsulfonyl group or a carbamoyl group, (2) a lower alkyl group or lower alkoxyl group which may be substituted by a halogen atom(s), a carboxyl group(s) or an aryl group(s), (3) a phenyloxy group which may be substituted by a lower alkoxycarbonyl group or a carboxyl group, $R^2$: a hydroxyl group, a lower alkoxyl group, an amino group or a mono- or di-lower alkylamino group, A: a lower alkylene group which may be substituted or a group represented by the formula —O—B—, and B: a lower alkylene group, with the proviso that the case wherein R represents an imidazolyl group, $R^1$ represents a cyano group, A represents an ethylene group and $R^2$ represents a hydroxyl group is excluded; or a tautomer thereof, a salt thereof, a hydrate thereof or a solvate thereof. The present invention also provides a glutamate receptor antagonist comprises as an effective ingredient the 1,2,3,4-tetrahydroqunoxalinedione derivative or a pharmaceutically acceptable salt thereof. More specifically, the present invention provides a compound which has a NMDA-glycine receptor antagonizing action and/or AMPA receptor antagonizing action, or inhibitory activity of kainate-induced neurotoxicity and is useful as an anti-ischemia or as a psychotropic. The present invention further provides a pharmaceutical composition which comprises 1,2,3,4-tetrahydroquinoxalinedione derivative or a salt thereof and a pharmaceutically acceptable carrier.

Hereinafter, the compound represented by the above general formula (I) will be described in detail.

In the definition of the general formula, the term "lower" as used herein means a linear or branched carbon chain having 1 to 6 carbon atoms, unless otherwise specified.

Illustrative examples of the "lower alkyl group" include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like. Preferred is an alkyl group having 1 to 3 carbon atoms.

The term "mono- or di-lower alkylamino group" as used herein means an amino group substituted by one or two lower alkyl groups exemplified above. The illustrative examples include mono-lower alkylamino groups such as methylamino, ethylamino, propylamino, isopropylamino, butylamino, isobutylamino, sec-butylamino, tert-butylamino, pentyl(amyl)amino, isopentylamino, neopentylamino and tertpentylamino group; and di-lower alkylamino groups such as dimethylamino, ethylmethylamino, diethylamino, dipropylamino, diisopropylamino, dibutylamino and diisobutylamino groups. Among them, amino, methylamino, ethylamino, dimethylamino and diethylamino groups are preferred.

Illustrative examples of the "lower alkanoyl group" include formyl, acetyl, propionyl, isopropionyl, butyryl, isobutyryl, valeryl, isovaleryl, pivaloyl, hexanoyl groups and the like.

The term "lower alkylthio group" as used herein means the above-described thiol group whose hydrogen atom has been substituted by a lower alkyl group. The illustrative examples include methylthio, ethylthio, propylthio, isopropylthio, butylthio, isobutylthio, sec-butylthio, tert-butylthio, pentyl(amyl)thio, isopentylthio, neopentylthio, tert-pentylthio, 1-methylbutylthio, 2-methylbutylthio, 1,2-dimethylpropylthio, hexylthio, isohexylthio, 1-methylpentylthio, 2-methylpentylthio, 3-methylpentylthio, 1,1-dimethylbutylthio, 1,2-dimethylbutylthio, 2,2-dimethylbutylthio, 1,3-dimehtylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, 1-ethyl-2-methylpropylthio groups and the like. Preferred is an alkylthio group having 1 to 3 carbon atoms.

Illustrative examples of the "lower alkylsulfinyl group" include methylsulfinyl, ethylsulfinyl, propylsulfinyl, isopropylsulfinyl, butylsulfinyl, isobutylsulfinyl, sec-butylsulfinyl, tert-butylsulfinyl, pentyl(amyl)sulfinyl, isopentylsulfinyl, neopentylsulfinyl, tert-pentylsulfinyl, 1-methylbutylsulfinyl, 2-methylbutylsulfinyl, 1,2-dimethylpropylsulfinyl, hexylsulfinyl, isohexylsulfinyl, 1-methylpentylsulfinyl, 2-methylpentylsulfinyl, 3-methylpentylsulfinyl, 1,1-dimethylbutylsulfinyl, 1,2-dimethylbutylsulfinyl, 2,2-dimethylbutylsulfinyl, 1,3-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl, 1-ethyl-2-methylpropylsulfinyl groups and the like. Preferred is an alkylsulfinyl group having 1 to 3 carbon atoms.

Illustrative examples of the "lower alkylsulfonyl group" include methylsulfonyl, ethylsulfonyl, propylsulfonyl, isopropylsulfonyl, butylsulfonyl, isobutylsulfonyl, sec-butylsulfonyl, tert-butylsulfonyl, pentyl(amyl)sulfonyl, isopentylsulfonyl, neopentylsulfonyl, tert-pentylsulfonyl, 1-methylbutylsulfonyl, 2-methylbutylsulfonyl, 1,2-dimethylpropylsulfonyl, hexylsulfonyl, isohexylsulfonyl, 1-methylpentylsulfonyl, 2-methylpentylsulfonyl, 3-methylpentylsulfonyl, 1,1-dimethylbutylsulfonyl, 1,2-dimethylbutylsulfonyl, 2,2-dimethylbutylsulfonyl, 1,3-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl, 1-ethyl-2-methylpropylsulfonyl group and the like. Preferred is an alkylsulfonyl group having 1 to 3 carbon atoms.

Examples of the "lower alkoxyl group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy groups and the like. Among them, methoxy, ethoxy, propoxy and isopropoxy groups are preferred.

The above-exemplified lower alkyl or lower alkoxyl group may be substituted at any position with at least one substituent selected from a halogen atom, carboxyl group or an aryl group.

Illustrative examples of such a substituted-lower alkyl or lower alkoxyl group include trihalogeno-lower alkyl, carboxy-lower alkyl, carboxy-lower alkoxyl, aryl-lower alkoxyl groups and the like. Preferred are trihalogenomethyl, carboxymethoxy and benzyloxy groups. The aryl group which is a substituent may be further substituted by a halogen atom or a carboxyl group. As such an example, a carboxybenzyloxy group may be mentioned.

The term "halogen atom" as used herein means a fluorine, chorine, bromine or iodine atom.

The term "aryl group" as used herein illustratively means a carbocyclic aryl group. Examples include phenyl, naphthyl, anthryl, phenanthryl groups and the like.

Examples of the "lower alkylene group" in A or B include linear or branched alkylene groups having 1 to 6 carbon atoms. The illustrative examples include methylene, ethylene, trimethylene, methylmethylene, dimethylmethylene, 1-methylethylene, 2-methylethylene, tetramethylene 1-methyltrimethylene, 2-methyltrimethylene, 3-methyltrimethylene, 1-ethylethylene, 2-ethylethylene, 2,2-dimethylethylene, 1,1-dimethylethylene, ethylmethylmethylene, pentamethylene, 1-methyltetramethylene, 2-methyltetramethylene, 3-methyltetramethylene, 4-methyltetramethylene, 1,1-dimethyltrimethylene, 2,2-dimethyltrimethylene, 3,3-dimethyltrimethylene, 1,3-dimethyltrimethylene, 2,3-dimethyltrimethylene, 1,2-dimethyltrimethylene, 1,1,2-trimethylethylene, diethylmethylene, hexamethylene, 1-methylpentamethylene, 1,1-dimethyltetramethylene, 2,2-dimethyltetramethylene, 1,3-dimethyltetramethylene, 1,4-dimethyltetramethylene groups and the like.

Examples of the substituent in the "lower alkylene group which may be substituted" include a phenyl group which may be substituted by a nitro group. Illustrative examples thereof include phenyl, 4-nitrophenyl, 3-nitrophenyl, 2-nitrophenyl groups and the like, and a 4-nitrophenyl group is preferred.

Among the groups represented by R, an imidazolyl group is preferred. As a group represented by $R^1$, following atoms or groups are preferred:

(1) a halogen atom, a nitro group, a cyano group, a mono- or di-lower alkylamino group, a lower alkylsulfinyl group, a lower alkylsulfonyl group or a carbamoyl group, (2) a lower alkyl or lower alkoxyl group which may be substituted by a carboxyl group or an aryl group, and (3) a phenyloxy group which may be substituted by a lower alkoxycarbonyl group.

More preferred is a compound wherein R represents a 1-imidazolyl group, X is a group represented by the formula CH, and $R^1$ represents a halogen atom, a nitro group, a trifluoromethyl group, a cyano group or a benzyloxy group. Particularly preferred compounds are:

2-[2,3-dioxo-7-(1H-imidazol-1-yl)-6-nitro-1,2,3,4-tetrahydroquinoxalin-1-yl]acetic acid or salt thereof;

2-[2,3-dioxo-7-(1H-imidazol-1-yl)-6-trifluoromethyl-1,2,3,4-tetrahydroquinoxalin-1-yl]acetic acid or salt thereof; and 2-[6-benzyloxy-2,3-dioxo-7-(1H-imidazol-1-yl)-1,2,3,4-tetrahydroquinoxalin-1-yl]acetic acid or salt thereof.

The compound (I) of the present invention has a tautomer based on a diketoquinoxaline skeleton. In addition, there exists an optical isomer (optically active substance, diastereomer or the like) depending on the kind of the group. These isomers in separated forms or mixtures of the isomers are included in the present invention.

The compound (I) of the present invention forms a salt with an acid or a base. Examples of the salt with an acid include acid addition salts with an inorganic acid, for example, mineral acid such as hydrochloric acid, hydrobromic acid, hydroiodic acid, sulfuric acid, nitric acid or phosphoric acid and those with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid or glutamic acid.

Examples of the salt with a base include salts with a an inorganic base such as sodium, potassium, magnesium, calcium or aluminum, salts with an organic base such as methylamine, ethylamine or ethanolamine, salts with a basic amino acid such as lysine, arginine or ornithine, and ammonium salts. In addition, the compound (I) of the present invention can form a hydrate, solvate with ethanol, or polymorphism.

(Preparation Methods)

The compound of the present invention can be prepared in accordance with the process shown by the following reaction scheme:

Method 1    Method 2    Method 3

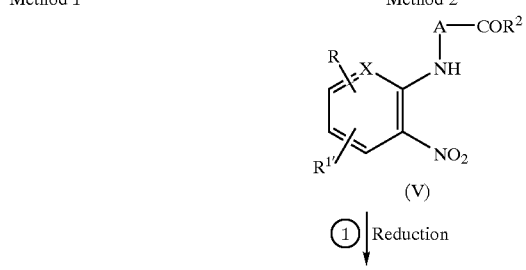

-continued

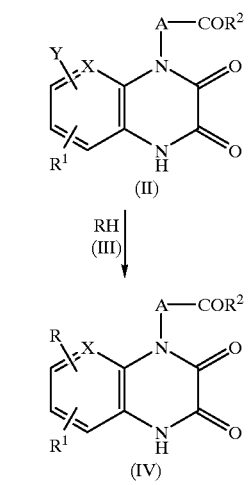
(II)

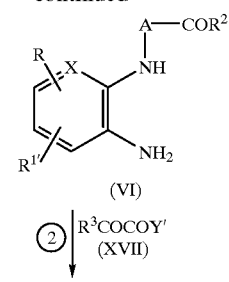
(VI)

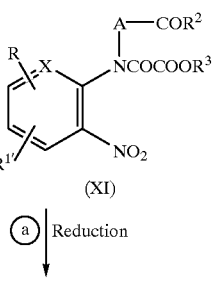
(XI)

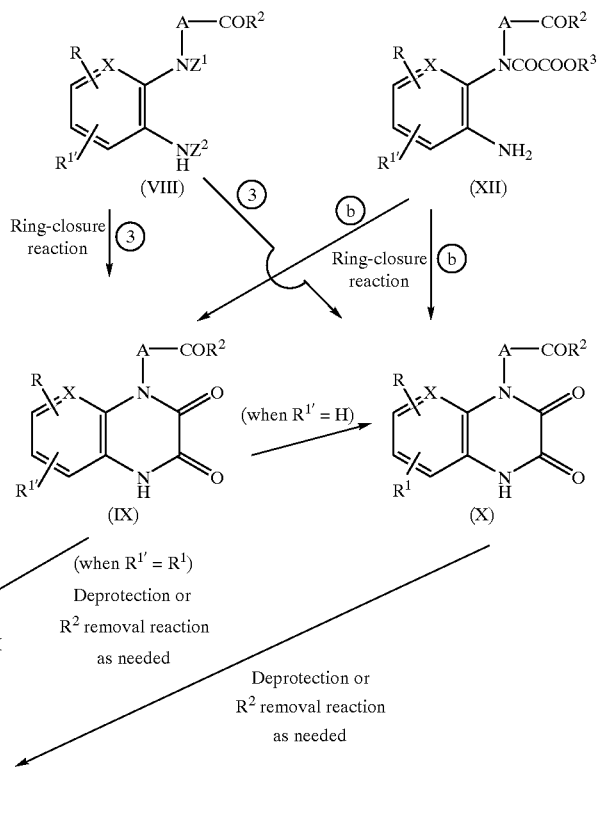

wherein X, A, $R^1$ and $R^2$ have the same meanings as defined above.

Y: a halogen atom $Y^1$: a halogen atom other than a fluorine atom $R^{1'}$: a hydrogen atom and a group represented by the above $R^1$, $R^3$: a lower alkyl group, $Z^1$, $Z^2$: a hydrogen atom and a group represented the formula $R^3COCO—$, with the proviso that both of $Z^1$ and $Z^2$ are not hydrogen atoms at the same time.

In the above formula, examples of the halogen atom include fluorine, chlorine, bromine and iodine atoms.

When the compound has OH as $R^2$, a compound protected with a protective group for a carboxyl group can be used.

Examples of the protected carboxyl group and its equivalent include esters, amides and orthoesters; and also the derivatives exemplified in "*Protective Groups in Organic Synthesis,* 2nd ed., edited by T. W. Greene and P. G. M. Wuts, John Wiley & Sons, INC., Chapter 5 (1990)"

Method 1

The compound (I) or (IV) of the present invention can be obtained by reacting a halogen compound (II) and an imidazole (III) in an amount corresponding to the reaction at −10° C. to 150° C., preferably at 20° C. to 120° C. in a solvent or without solvent under stirring.

The reaction is generally carried out under heating in a solvent such as dimethylformamide (DMF), dimethylsulfoxide (DMSO), acetonitrile, acetone or tetrahydrofuran (THF). To accelerate the reaction, a base such as sodium hydroxide or potassium hydroxide, or a copper salt may be added.

The compound (I) of the present invention can also be obtained by subjecting the compound (IV) to deprotection or $R^2$ removal reaction in a manner known in the art.

The deprotection or $R^2$ removal reaction can be carried out in accordance with the method shown in the above-described book edited by T. W. Greene, et al. or in a manner known in the art.

For example, hydrolysis can be employed. Examples of hydrolysis include acid hydrolysis carried out in the presence of hydrochloric acid or the like and alkali saponification carried out in the presence of a base such as sodium hydroxide.

Method 2

The compound (I), (IX) or (X) of the present invention can be obtained by the following process:

(1) A nitroaniline or nitroaminopyridine compound (V) is reduced, whereby a diamine compound (VI) is obtained.

(2) The diamine compound (VI) is reacted with an oxalate halide (VII), whereby an amide compound (VIII) and a mixture thereof are obtained.

(3) The amide compound (VIII) and a mixture thereof are subjected to ring-closure reaction, whereby a quinoxalinedione compound or pyridopyrazinedione compound (IX) or (X) is obtained.

(4) The quinoxalinedione compound or pyridopyrazinedione compound (IX) is subjected to known aromatic substitution reaction, whereby a substituted quinoxalinedione compound or pyridopyrazinedione compound (X) is obtained.

(5) Deprotection or $R^2$ removal reaction is carried out in accordance with the method 1.

The representative steps processes for the aforementioned (1) to (4) are described below.

Examples of the reduction reaction in (1) include catalytic reduction using, for example, Raney nickel or palladium-carbon in a manner known in the art; and metal reduction using iron powder or zinc dust.

Examples of the amidation reaction in (2) include the reaction between the diamine compound (VI) and an oxalate halide (VII) in an amount corresponding to the reaction in a solvent of chloroform or THF at −10° C. to 60° C., preferably 0° C. to room temperature.

It is preferred to add an alkali such as triethylamine in order to accelerate the reaction.

The ring-closure reaction in (3) is carried out, for example, by heating the amide compound (VIII) and a mixture thereof in the above-described solvent or by heating in the presence of an acid catalyst such as hydrochloric acid. Examples of the aromatic substitution reaction in (4) in the case where $R^{1\prime}$ of the compound (IX) represents a hydrogen atom include the method of causing nitric acid or salt thereof on the quinoxalinedione compound or pyridopyrazinedione compound (IX) in sulfuric acid, acetic anhydride-acetic acid, or sulfuric acid-acetic anhydride-acetic acid; and the method of causing reaction between the quinoxalinedione compound or pyridopyrazinedione compound and nitronium tetrafluoroborate in an organic solvent such as sulfolane or acetonitrile at 0° C. to under heating.

Method 3

The compound (I), (IX) or (X) of the present invention can be obtained by the following process:

a) A nitroanilide compound is reduced as described in (2) of the method 2, whereby an aminoanilide compound (XII) is obtained.

b) The aminoanilide compound (XII) is subjected to ring-closure reaction as described in (3) of the method 2, whereby a quinoxalinedione compound (IX) or (X) is obtained.

The subsequent process to obtain the compound (I) of the present invention is performed in accordance with the second preparation process.

The compound having a nitro group as $R^1$ can be obtained, for example, by subjecting the quinoxalinedione compound (IX) wherein $R^1$ is a hydrogen atom to nitration reaction in accordance with (4) of the method 2.

Method 4

The compound having an amino group as $R^1$ can be obtained by subjecting the compound having a nitro group as $R^1$ to reduction reaction as described in (2) of the method 2. Alternatively, it can be obtained by deprotection reaction using a protected amino group as $R^1$ in the method 2 or 3 in a manner known in the art.

The compound having a mono- or di-lower alkylamino group as $R^1$ can be obtained by reacting a compound having an amino group as $R^1$ with a halogeno-lower alkyl compound as described in the method 1. Alternatively, it can be obtained by reacting an aldehyde compound (such as formalin) with an amine compound in a solvent or without solvent, preferably in the presence of an acid, under the conditions to which (1) of the method 2 belongs.

Method 5

The compound having as $R^2$ an amino group or a mono- or di-lower alkylamino group can be obtained by the amidation reaction of a carboxy compound (I) in a manner known in the art.

Alternatively, it can be obtained by the ester-amide exchange reaction between the ester compound (IV), (IX) or (X) and a corresponding amine or ammonia.

As an amidation reaction of the carboxy compound (I), for example, it is converted into acid chloride using, for example, thionyl chloride, followed by the addition of the corresponding amount of amine or ammonia.

The ester-amide exchange reaction is carried out, for example, between an ester compound and concentrated aqueous ammonia at −10° C. to room temperature.

Method 6

The compound (II) having an alkyleneoxy group as A can be obtained by reacting a corresponding hydroxyquinoxaline-2,3-dione with a corresponding alkylating agent in the presence of a base. The reaction can be carried out generally in a solvent such as DMF, DMSO, THF, acetonitrile or acetone. It is preferred to use an organic base (e.g., potassium carbonate or sodium hydride) as a base.

Method 7

The compound (I) which has a carbamoyl group as $R^1$ can be obtained in a manner known in the art by treating a corresponding derivative (I) which has a cyano group as $R^1$ under acid conditions or basic conditions. For example, it can be obtained by reacting a cyano derivative with an acid such as hydrochloric acid, sulfuric acid or formic acid or reacting under basic conditions such as in an aqueous solution of hydrogen peroxide or sodium hydroxide.

The invention compound so prepared is isolated and purified as a free compound or its salt.

Isolation and purification are carried out by the ordinary chemical operation such as extraction, concentration, evaporation, crystallization, filtration, recrystallization, various kinds of chromatography, or the like.

The compound of the present invention has high affinity with the AMPA receptor and exhibited potent activities in the inhibitory action against kainic acid neurotoxicity and anticonvulsant effect for audiogenic seizure in DBA/2 mouse.

Accordingly, based on this action, the compound of the present invention is a particularly useful pharmaceutical as a psychotropic for the prevention and treatment of Huntington chorea, Parkinson disease, epilepsy, Alzheimer disease or senile dementia; and also such as an anti-ischemia agent for the prevention and treatment of cell death caused by cerebral ischemia, oxygen deficiency or the temporary cardiac arrest, neurodegeneration observed after hypoglycemia or seizure, and deficiency of mental and motor function.

Testing method

Inhibitory activity against the binding with [$^3$H]-AMPA, kainic acid neurotoxicity and audiogenic seizure were confirmed as follows:

1) Measurement of inhibitory activity against the binding of [$^3$H]-AMPA:

On ice water, 0.5 ml in total of a reaction liquid containing about 45 nM [$^3$H]-AMPA [2-amino-3-(3-hydroxy-5-methyl-4-isoxazolyl)propionic acid], about 300 mg of a sample of a rat cerebral membrane and a test compound was reacted for 45 minutes. The amount of [$^3$H]-AMPA bound to the AMPA receptor was measured by the filtration method. A portion substituted by 10 μM quisqualic acid in the total bound amount was taken as the specific binding amount. Evaluation of the test compound was carried out by determining the binding inhibition ratio against the specific binding. As a result, for example, the Ki value of the compound of Example 1 was 0.73 μM, that of the compound of Example 9 was 0.093 μM and that of the compound of Example 19 was 0.070 μM, which are potent.

2) Measurement of inhibitory activity against kainic acid neurotoxicity:

Inhibitory action of the invention compound against kainic acid neurotoxicity was investigated using the primary culture system of the hippocampal neuron of a fetal rat.

(1) Incubation conditions

The hippocamp was cut out from a brain of the 18 to 20-day-old fetal rat and was subjected to enzyme treatment with papain and DNase I to disperse the cells. The cells so obtained were floated on MEM containing 10% serum and then were inoculated on a 48-well plate treated in advance with poly-I-lysine in a concentration of $4 \times 10^5$ cell/cm$^2$. Twenty four hours later, the serum was replaced by a serum-free medium. The medium replacement was carried out twice a week. The cells which were cultivated for at least 6 days were provided for the following test.

(2) Inhibition against kainic acid neurotoxicity

Neurotoxicity was expressed by an activity of lactate dehydrogenase released in the culture medium by the cell death. As a control, neurons which were exposed to a serum-free medium containing 300 μM kainic acid for 24 hours were used. Each compound, together with 300 μM kainic acid, was allowed to act on the neuron for 24 hours and inhibitory action of each compound against neuronal death caused by kainic acid was evaluated.

As the result, for example, the compound of Example 1 had IC$_{50}$ of 0.8 μM, the compound of Example 9 had IC$_{50}$ of 0.96 μM and the compound of Example 19 had IC$_{50}$ of 0.48 μM, which are potent.

3) Measurement of audiogenic seizure inhibitory action in DBA/2 mouse

Ten male 21 to 28-day-old mice were exposed to auditory and stimulation by the sound of 12 kHz and 120 dB in a sound proof box for one minute or until these mice cause tonic seizure. The test compound was suspended in a 0.5% methylcellulose solution or dissolved in physiological saline and the resulting suspension or solution was intraperitoneally administered 15 minutes before the stimulation by the sound. The drug efficacy was evaluated by presence or absence of the appearance of seizure and the minimum effective dose (MED) was determined.

As a result, the compound of Example 1, the compound of Example 9 and the compound of Example 19 suppressed the audiogenic seizure in an amount of 3 mg/kg, 10 mg/kg and 1 mg/kg, respectively.

4) Measurement of solubility

Preparation of Buffer:

To a 0.1M aqueous solution of potassium dihydrogenphosphate, a 0.1M aqueous solution of sodium dihydrogenphosphate was added, whereby buffers having pH of 5, 6, 7 and 8 were prepared, respectively.

Measurement of Solubility:

About 5 mg portions of the invention compound were weighed precisely in four glass test tubes and 0.1 ml phosphate buffers having pH 5, 6, 7 and 8 were added, respectively, followed by thorough shaking. The value obtained in accordance with the following equation was taken as the solubility.

$$\text{Solubility (mg/ml) of the invention compound} = \frac{\text{weighed value (mg) of the invention compound}}{\text{Volume (ml) of phosphate buffer used for dissolution of invention compound}}$$

The results are shown in Table 1. The compound of Example 9 showed the solubility of 4,100 μg/ml at pH 6. Thus, the compound of the invention showed high solubility even at the neutral point or in the vicinity of neutral point. Accordingly, the compound of the present invention can be easily formulated into an oral preparation such as tablets and capsules or a parenteral preparation such as injection so that it is a markedly useful compound.

In addition, the compound of the present invention has high and therefore excellent solubility in blood even at the clinical administration and does not precipitate easily in the organs, so that is has high utility.

|  | pH 5 | pH 6 | pH 7 | pH 8 |
| --- | --- | --- | --- | --- |
| Example 1 | 2489 (μg/ml) | 2621 | 3641 | 5130 |

A pharmaceutical preparation containing one or more compounds of the present invention or salts thereof as an effective ingredient is prepared using a carrier or excipient and other additives ordinarily used for the formulation.

The carrier or excipient for pharmaceutical preparations may be either solid or liquid, such as lactose, magnesium stearate, starch, talc, gelatin, agar, pectin, gum arabic, olive oil, sesame oil, cacao butter and ethylene glycol and other conventional carriers or excipients.

As a solid composition for the oral administration according to the present invention, tablets, powders, granules or the like may be used. In such a solid composition, one or more active substances are mixed with at least one inert diluent such as lactose, mannitol, glucose, hydroxypropylcellulose, microcrystalline cellulose, starch, polyvinyl pyrrolidone or aluminum magnesium metasilicate. The composition may contain an additive other than the inactive diluent, for example, a lubricant such as magnesium stearate, disintegrator such as calcium cellulose glycolate, stabilizer such as lactose, or solubilizing agent or solubilizing assistant such as glutamic acid or aspartic acid. The tablet or pill may be coated with a film made of a gastric or enteric substance such as sucrose, gelatin, hydroxypropylcellulose or hydroxypropylmethylcellulose phthalate.

Examples of the liquid composition for the oral administration include a pharmaceutically acceptable emulsion, solution, suspension, syrup or elixir and it contains a generally employed inactive diluent such as purified water or ethanol. In addition to the inactive diluent, the liquid composition may also contain an adjuvant such as solubilizing agent or solubilizing assistant, wetting agent or suspending agent, a sweetener, a flavoring agent, an aroma or an antiseptic.

Examples of the injections for parenteral administration include sterile aqueous or nonaqueous solution, suspension and emulsion. As a diluent for aqueous solution or suspension, injection-grade distilled water and physiological saline are included. Examples of the diluent for nonaqueous solution or suspension include propylene glycol, polyethylene glycol, vegetable oil such as olive oil, alcohol such as ethanol and "Polysolbate 80" (trade name). Such a composition may further contain an additive such as an isotonicity agent, antiseptic, wetting agent, emulsifying agent, dispersing agent, stabilizing agent (e.g., lactose), or solubilizing agent or solubilizing assistant. They are sterilized, for example, by filtration through a bacteria-retaining filter, incorporation of an insecticide, or irradiation. The injection can also be obtained by first preparing a sterile solid composition and then dissolving it in a sterile water or sterile injection-graded solvent upon use.

Administration may be carried out in any form such as oral administration by tablets, pills, capsules, granules, powders or liquid; or parenteral administration by injections such as intravenous injection or intramuscular injection, suppositories or transdermal administration. The dose is determined appropriately according to each case in consideration of the symptoms, age or sex of the patient to be administered. The general dose ranges from 1 to 1000 mg/day, preferably 50 to 200 mg/day, per adult once a day or in several portions in the case of oral administration, or 1 mg to 500 mg a day per adult once a day or in several portions in the case of intravenous administration or in the case of continuous intravenous administration within a range of 1 hour/day to 24 hours/day. As described above, the dose may vary depending on various conditions, so it is needless to say that the dose smaller than the above range may sometimes be sufficient.

EXAMPLES

Hereinafter, the present invention will be described in further detail by way of Examples. It should however borne in mind that the present invention is not limited to or by the following Examples. Incidentally, the preparation examples of the main raw material compounds used in the Examples will also be described.

Example 1

1) To a mixture of 13.96 g of a glycine ethyl ester hydrochloride, 30 ml of THF, 10.11 g of triethylamine and 30 ml of DMF, 15.91 g of 2,4-difluoronitrobenzene was added, followed by heating under reflux for 3 hours under an argon gas stream. After cooling of the reaction mixture and dilution with ethyl acetate, the insoluble matter precipitated was removed by filtration. The filtrate was concentrated under reduced pressure. The resulting residue was dissolved in ethyl acetate, washed successively with water and brine, and then dried over anhydrous sodium sulfate, followed by concentration under reduced pressure. The resulting residue was recrystallized from ethanol to give 17.32 g (71.5%) of N-(2-nitro-5-fluorophenyl)glycine ethyl ester.

Mass analysis (m/z): 242 (M$^+$)

Nuclear magnetic resonance spectrum (CDCl$_3$, TMS internal standard):

δ: 1.33 (3H, t, J=6.5 Hz), 4.04 (2H, d, J=4.9 Hz), 4.31 (2H, q, J=6.5 Hz), 6.34 (1H, dd, J=2.4, 11.0 Hz), 6.44 (1H, m), 8.25 (1H, dd, J=6.1, 9.7 Hz), 8.55 (1H, s).

2) A mixture of 6.52 g of N-(2-nitro-5-fluorophenyl) glycine ethyl ester, 100 ml of THF, 50 ml of methanol and 500 mg of 10% palladium-carbon was stirred in a hydrogen gas atmosphere, whereby the nitro group was reduced. The reaction mixture was filtered and the filtrate was concentrated under reduced pressure. To the resulting residue, 200 ml of chloroform and 7.54 ml of triethylamine were added to dissolve the former in the latter. While stirring, a 30 ml chloroform solution of 7.35 g of ethyl chloroglyoxylate was added dropwise to the resulting mixture under an argon gas stream under ice cooling. After the dropwise addition, stirring was carried out for 1 hour at room temperature, followed by dilution with chloroform. The diluted solution was washed successively with water, a saturated aqueous solution of sodium bicarbonate, a saturated aqueous solution of ammonium chloride and brine, and was dried over anhydrous sodium sulfate, followed by concentration under reduced pressure. To the resulting residue, 150 ml of ethanol and 1 ml of concentrated hydrochloric acid were added, followed by heating under reflux for 1 hour. After cooling, the resulting crystals were collected by filtration and dried under reduced pressure to give 5.80 g (80%) of ethyl 2-(7-fluoro-2,3-dioxo-1,2,3,4-tetrahydroquinoxalin-1-yl) acetate.

Mass analysis (m/z): 266 (M$^+$)

Nuclear magnetic resonance spectrum (DMSO-d$_6$, TMS internal standard):

δ: 1.22 (3H, t, J=7.3 Hz), 4.17 (2H, q, J=7.3 Hz), 4.95 (2H, s), 7.70 (1H, m), 7.22 (1H, dd, J=5.4, 8.8 Hz), 7.36 (1H, dd, J=2.4, 11.2 Hz), 12.20 (1H, s)

3) In 15 ml of concentrated sulfuric acid, under below 0° C., 1.20 g of ethyl 2-(7-fluoro-2,3-dioxo-1,2,3,4-tetrahydroquinoxalin-1-yl)acetate were added to dissolve the latter in the former. While stirring, 0.21 ml of fuming nitric acid (d=1.52) was added dropwise to the resulting solution and they were stirred at the same temperature for 30 minutes. The reaction mixture was poured into ice water. The crystals so precipitated were collected by filtration, washed with water and then, dried under reduced pressure to give 1.35 g (96%) of ethyl 2-(7-fluoro-6-nitro-2,3-dioxo-1, 2,3,4-tetrahydroquinoxalin-1-yl)acetate.

Mass analysis (m/z): 312 (M$^+$+1)

Nuclear magnetic resonance spectrum (DMSO-d$_6$, TMS internal standard):

δ: 1.24 (3H, t, J=7.3 Hz), 4.18 (2H, q, J=7.3 Hz), 5.02 (2H, s), 7.74 (1H, d, J=13.5 Hz), 7.95 (1H, d, J=7.3 Hz), 12.4 (1H, s).

4) A mixture of 928 mg of ethyl 2-(2,3-dioxo-7-fluoro-6-nitro-1,2,3,4-tetrahydroquinoxalin-1-yl)acetate, 450 mg of imidazole and 10 ml of DMF was stirred at 120° C. for 6 hours. After cooling, the reaction mixture was poured into ice water. The resulting crystals were collected by filtration, washed with water and then, dried under reduced pressure.

The resulting compound was added to 5 ml of a 1N aqueous solution of sodium hydroxide at room temperature, followed by stirring for 15 minutes to hydrolyze the ester. The reaction mixture was adjusted to about pH 3.5 with 1N hydrochloric acid. The crystals so precipitated were collected by filtration, washed with water and then dried under reduced pressure to give 473 mg (40%) of 2-[2,3-dioxo-7-(1H-imidazol-1-yl)-6-nitro-1,2,3,4-tetrahydroquinoxalin-1-yl]acetic acid•1 hydrochloride•1.2 hydrate.

Melting point: 225° C. (decomposition)

Ellemental analysis for C$_{13}$H$_9$N$_5$O$_6$ . HCl . 1.2H$_2$O

| | C(%) | H(%) | N(%) | Cl(%) |
|---|---|---|---|---|
| Calculated: | 40.11 | 3.21 | 17.99 | 9.11 |
| Found: | 40.01 | 3.11 | 17.86 | 9.02 |

Mass analysis (m/z): 332 (M$^+$+1)

Nuclear magnetic resonance spectrum (DMSO-d$_6$, TMS internal standard):

δ: 4.89 (2H, s), 7.88 (1H, s), 8.01 (1H, s), 8.08 (1H, s), 8.28 (1H, s), 9.43 (1H, s), 12.89 (1H,s), 13.1–14.2 (1H, bs).

Example 2

1) In a similar manner to Example 1–1) except for the use of 10.5 g of β-alanine methyl ester hydrochloride, 20 ml of THF, 7.58 g of triethylamine, 20 ml of DMF and 12.0 g of 2,4-difluoronitrobenzene, 14.58 g (80%) of methyl 3-(5-fluoro-2-nitrophenylamino)propionate was obtained.

Mass analysis (m/z): 242 (M$^+$)

Nuclear magnetic resonance spectrum (CDCl$_3$, TMS internal standard):

δ: 2.73 (2H, t, J=6.6 Hz), 3.61 (2H, t, J=6.6 Hz), 3.74 (3H, s), 6.36–6.42 (1H, m), 6.52 (1H, dd, J=2.9, 11.7 Hz), 8.22 (1H, dd, J=5.9, 9.3 Hz), 8.34 (1H, s).

2) In a similar manner to Example 1–2) except for the use of 6.19 g of methyl 3-(5-fluoro-2-nitrophenylamino) propionate, 5.84 g (55%) of ethyl 3-(2,3-dioxo-7-fluoro-1,2,3,4-tetrahydroquinoxalin-1-yl)propionate was obtained.

Mass analysis (m/z): 280 (M$^+$)

Nuclear magnetic resonance spectrum (DMSO-d$_6$, TMS internal standard):

δ: 1.27 (3H, t, J=6.8 Hz), 2.79 (2H, t, J=7.6 Hz), 4.18 (2H, q, J=6.8 Hz), 4.45 (2H, t, J=7.6 Hz), 6.94–6.99 (1H, m), 7.07 (1H, dd, J=2.4, 9.7 Hz), 7.30 (1H, dd, J=4.5, 9.7 Hz), 11.23 (1H, s).

3) In a similar manner to Example 1–3) except for the use of 1.50 g of ethyl 3-(2,3-dioxo-7-fluoro-1,2,3,4-tetrahydroquinoxalin-1-yl)propionate, 1.58 g (91%) of ethyl 3-(2,3-dioxo-7-fluoro-6-nitro-1,2,3,4-tetrahydroquinoxalin-1-yl)propionate was obtained.

Mass analysis (m/z): 326 (M$^+$+1)

Nuclear magnetic resonance spectrum (DMSO-d$_6$, TMS internal standard):

δ: 1.21 (3H, t, J=7.1 Hz), 2.67 (2H, t, J=7.3 Hz), 4.08 (2H, q, J=7.1 Hz), 4.32 (2H, t, J=13.3 Hz), 7.78 (1H, d, J=13.8 Hz), 7.89 (1H, d, J=7.3 Hz), 12.3 (1H, s).

4) In a similar manner to Example 1–4) except for the use of 1.20 g of ethyl 3-(7-fluoro-6-nitro-2,3-dioxo-1,2,3,4-tetrahydroquinoxalin-1-yl)propionate, 502 mg of imidazole and 10 ml of DMF, 704 mg (48%) of 3-[2,3-dioxo-7-(1H-imidazol-1-yl)-6-nitro-1,2,3,4-tetrahydroquinoxalin-1-yl] propionic acid•1 hydrochloride•1 hydrate was obtained.

Melting point: 281–282° C. (decomposition)

Elemental analysis for $C_{14}H_{11}N_5O_6 \cdot HCl \cdot H_2O$

|  | C(%) | H(%) | N(%) | Cl(%) |
|---|---|---|---|---|
| Calculated: | 42.07 | 3.53 | 17.52 | 8.87 |
| Found: | 41.98 | 3.78 | 17.63 | 8.65 |

Mass analysis (m/z): 346 (M$^+$+1)

Nuclear magnetic resonance spectrum (DMSO-d$_6$, TMS internal standard):

δ: 2.65 (2H, t, J=7.8 Hz), 4.29 (2H, t, J=7.8 Hz), 7.91 (1H, s), 8.05 (1H, s), 8.07 (1H, s), 8.25 (1H, s), 9.57 (1H, s), 12.72 (1H, s), 12.1–13.2 (1H, bs).

Example 3

1) In a similar manner to Example 1–1) except for the use of 9.55 g of ethyl γ-aminobutyrate hydrochloride, 20 ml of THF, 6.73 g of triethylamine, 10 ml of DMF and 9.45 g of 2,4-difluoronitrobenzene, 9.72 g (61%) of ethyl 4-(5-fluoro-2-nitrophenylamino)butyrate was obtained.

Mass analysis (m/z): 270 (M$^+$)

Nuclear magnetic resonance spectrum (CDCl$_3$, TMS internal standard):

δ: 1.28 (3H, t, J=7.0 Hz), 2.02–2.08 (2H, m), 2.47 (2H, q, J=7.1 Hz), 3.35 (2H, t, J=7.0 Hz), 4.17 (2H, t, J=6.0 Hz), 6.35–6.41 (1H, m), 6.52 (1H, dd, J=2.4, 11.6 Hz), 8.21 (1H, dd, J=5.1, 9.2 Hz).

2) In a similar manner to Example 1–2) except for the use of 6.43 g of ethyl 4-(5-fluoro-2-nitrophenylamino)butyrate, 5.93 g (85%) of ethyl 4-(2,3-dioxo-7-fluoro-1,2,3,4-tetrahydroquinoxalin-1-yl)butyrate was obtained.

Mass analysis (m/z): 294 (M$^+$)

Nuclear magnetic resonance spectrum (DMSO-d$_6$, TMS internal standard):

δ: 1.28 (3H, t, J=7.4 Hz), 2.04–2.10 (2H, m), 2.52 (2H, t, J=6.7 Hz), 4.18–4.26 (2H, m), 6.93–6.98 (1H, m), 7.26–7.35 (2H, m), 11.59 (1H, s).

3) In a similar manner to Example 1–3) except for the use of 2.64 g of ethyl 4-(2,3-dioxo-7-fluoro-1,2,3,4-tetrahydroquinoxalin-1-yl)butyrate, 2.81 g (92%) of ethyl 4-(2,3-dioxo-7-fluoro-6-nitro-1,2,3,4-tetrahydroquinoxalin-1-yl)butyrate was obtained.

Mass analysis (m/z): 340 (M$^+$+1)

Nuclear magnetic resonance spectrum (DMSO-d$_6$, TMS internal standard):

δ: 1.29 (3H, t, J=7.3 Hz), 1.98–2.05 (2H, m), 2.52 (2H, t, J=6.7 Hz), 4.15–4.24 (4H, m), 7.56 (1H, d, J=12.9 Hz), 8.03 (1H, d, J=6.7 Hz).

4) In a similar manner to Example 1–4) except for the use of 1.50 g of ethyl 4-(7-fluoro-6-nitro-2,3-dioxo-1,2,3,4-tetrahydroquinoxalin-1-yl)butyrate, 632 mg of imidazole and 10 ml of DMF, 1.42 g (80%) of 4-[2,3-dioxo-7-(1H-imidazol-1-yl)-6-nitro-1,2,3,4-tetrahydroquinoxalin-1-yl] butyric acid•1 hydrochloride•0.1 hydrate was obtained.

Melting point: >300° C.

Elemental analysis for $C_{15}H_{13}N_5O_6 \cdot HCl \cdot 0.1H_2O$

|  | C(%) | H(%) | N(%) | Cl(%) |
|---|---|---|---|---|
| Calculated: | 45.32 | 3.60 | 17.62 | 8.92 |
| Found: | 45.20 | 3.68 | 17.57 | 8.96 |

Mass analysis (m/z): 360 (M$^+$+1)

Nuclear magnetic resonance spectrum (DMSO-d$_6$, TMS internal standard):

δ: 1.86 (dt, J=6.8, 7.4 Hz), 2.38 (2H, t, J=6.8 Hz), 4.12 (2H, t, J=7.4 Hz), 7.92 (1H, s), 8.02 (1H, s), 8.07 (1H, s), 8.25 (1H, s), 9.56 (1H, s), 12.70 (1H, s), 11.8–12.6 (1H, bs).

Example 4

In a similar manner to Example 1, the compound of Example 4 was obtained.

1) By using 9.25 g of glycine ethyl ester hydrochloride, 10.55 g (66.3 mmol) of 2,5-difluoronitrobenzene, 35 ml of THF, 9.29 ml of triethylamine and 5 ml of DMF, 7.59 g (47%) of N-(4-fluoro-2-nitrophenyl)glycine ethyl ester was aobtained.

Nuclear magnetic resonance spectrum (CDCl$_3$, TMS internal standard):

δ: 1.32 (3H, t, J=7.4 Hz), 4.08 (2H, d, J=5.5 Hz), 4.29 (2H, q, J=7.4 Hz), 6.68 (1H, dd, J=4.3, 9.1 Hz), 7.24–7.29 (1H, m), 7.92 (1H, dd, J=3.0, 9.1 Hz), 8.27 (1H, bs).

2) A mixture of 7.41 g (30.6 mmol) of N-(4-fluoro-2-nitrophenyl)glycine ethyl ester, 120 ml of THF and 0.5 g of 10% palladium-carbon was stirred at room temperature under normal pressure in a hydrogen gas atmosphere. After the reaction, the catalyst was removed by filtration. To the filtrate, 150 ml of THF and 19.5 ml of triethylamine were added. Under ice cooling, a mixture of 19 g of ethyl chloroglyoxylate and 20 ml of THF was added dropwise to the resulting mixture, followed by stirring. The reaction mixture was heated to room temperature and was stirred overnight. The crystals so precipitated were removed by filtration and the filtrate was concentrated under reduced pressure. To the residue, 150 ml of ethanol and 1.5 ml of concentrated hydrochloric acid were added, followed by heating under reflux for 4 hours. After cooling, the crystals so precipitated were collected by filtration, washed with ethanol and dried under reduced pressure to give 6.77 g (83%) of ethyl 2-(2,3-dioxo-6-fluoro-1,2,3,4-tetrahydroquinoxalin-1-yl)acetate.

Nuclear magnetic resonance spectrum (DMSO-$d_6$, TMS internal standard):

δ: 1.22 (3H, t, J=7.3 Hz), 4.17 (2H, q, J=7.3 Hz), 4.97 (2H, s), 7.00 (1H, dd, J=3.0, 9.2 Hz), 7.02–7.06 (1H, m), 7.35 (1H, dd, J=4.9, 9.2 Hz), 12.25 (1H, s).

3) By using 2.45 g (9.21 mmol) of 2-(2,3-dioxo-6-fluoro-1,2,3,4-tetrahydroquinoxalin-1-yl)acetate, 15 ml of concentrated sulfuric acid and 0.5 ml of fuming nitric acid, 2.74 g (96%) of ethyl 2-(2,3-dioxo-6-fluoro-7-nitro-1,2,3,4-tetrahydroquinoxalin-1-yl)acetate was obtained.

Nuclear magnetic resonance spectrum (DMSO-$d_6$, TMS internal standard):

δ: 1.23 (3H, t, J=6.7 Hz), 4.19 (2H, q, J=6.7 Hz), 5.05 (1H, s), 7.19 (1H, d, J=11.6 Hz), 8.10 (1H, d, J=6.7 Hz), 12.68 (1H, s).

4) By using 2.02 g of ethyl 2-(2,3-dioxo-6-fluoro-7-nitro-1,2,3,4-tetrahydroquinoxalin-1-yl)acetate, 1.33 g of imidazole and 15 ml of DMF, 2.24 g (96%) of ethyl 2-[2,3-dioxo-6-(1H-imidazol-1-yl)-7-nitro-1,2,3,4-tetrahydroquinoxalin-1-yl]acetate was obtained.

Nuclear magnetic resonance spectrum (DMSO-$d_6$, TMS internal standard):

δ: 1.25 (3H, t, J=7.3 Hz), 4.21 (2H, q, J=7.3 Hz), 5.09 (1H, s), 7.11 (1H, s), 7.26 (1H, s), 7.45 (1H, s), 7.93 (1H, s), 8.21 (1H, s), 12.3–13.0 (1H, bs).

5) By using 2.09 g (5.80 mmol) of ethyl 2-[2,3-dioxo-6-(1H-imidazol-1-yl)-7-nitro-1,2,3,4-tetrahydroquinoxalin-1-yl]acetate and 10 ml of a 1N aqueous solution of sodium hydroxide, 1.88 g (84%) of 2-[2,3-dioxo-6-(1H-imidazol-1-yl)-7-nitro-1,2,3,4-tetrahydroquinoxalin-1-yl]acetic acid•1 hydrochloride•1 hydrate was obtained.

Melting point: 217–218° C.

Elemental analysis for $C_{13}H_9N_5O_6 \cdot HCl \cdot H_2O$

|  | C(%) | H(%) | N(%) | Cl(%) |
|---|---|---|---|---|
| Calculated: | 40.48 | 3.14 | 18.16 | 9.19 |
| Found: | 40.17 | 3.04 | 18.08 | 9.20 |

Example 5

1) A mixture of 1.30 g of ethyl 2-[2,3-dioxo-7-(1H-imidazol-1-yl)-6-nitro-1,2,3,4-tetrahydroquinoxalin-1-yl]acetate, 80 ml of THF, 20 ml of methanol and 600 mg of 10% palladium-carbon was stirred in a hydrogen gas atmosphere for 36 hours. The reaction mixture was filtered and the filtrate was concentrated under reduced pressure to give 1.02 g (86%) of ethyl 2-[6-amino-2,3-dioxo-7-(1H-imidazol-1-yl)-1,2,3,4-tetrahydroquinoxalin-1-yl]acetate.

Nuclear magnetic resonance spectrum (DMSO-$d_6$, TMS internal standard):

δ: 1.14–1.22 (3H, m), 4.09–4.18 (2H, m), 4.88 (2H, s), 5.05 (2H, s), 6.71 (1H, s), 7.11 (1H, s), 7.16 (1H, s), 7.30 (1H, s), 7.74 (1H, s), 12.11 (1H, s).

2) To 1.5 ml of a 1N aqueous solution of sodium hydroxide, 150 mg of ethyl 2-[6-amino-2,3-dioxo-7-(1H-imidazol-1-yl)-1,2,3,4-tetrahydroquinoxalin-1-yl]acetate was added at room temperature, followed by stirring for 2 hours. The reaction mixture was adjusted to about pH 6 with 1N hydrochloric acid. The crystals so precipitated were collected by filtration, washed with water and then dried under reduced pressure to give 112 mg (74%) of 2-[6-amino-2,3-dioxo-7-(1H-imidazol-1-yl)-1,2,3,4-tetrahydroquinoxalin-1-yl]acetic acid•1.7 hydrate.

Melting point: >300° C.

Mass analysis (m/z): 302 (M$^+$+1)

Nuclear magnetic resonance spectrum (DMSO-$d_6$, TMS internal standard):

δ: 4.78 (2H, s), 5.04 (2H, br), 6.71 (1H, s), 7.11 (2H, s), 7.29 (1H, s), 7.73 (1H, s), 12.09 (1H, s).

Example 6

To 6 ml of aqueous ammonia, 100 mg of ethyl 2-[2,3-dioxo-7-(1H-imidazol-1-yl)-6-nitro-1,2,3,4-tetrahydroquinoxalin-1-yl]acetate was added at −5° C., followed by stirring at 0° C. for 3 hours and concentration under reduced pressure. The concentrate was washed with water and dried under reduced pressure to give 90 mg (89%) of 2-[2,3-dioxo-7-(1H-imidazol-1-yl)-6-nitro-1,2,3,4-tetrahydroquinoxalin-1-yl]acetamide•0.5 ammonia•1.3 hydrate.

Melting point: 245° C. (decomposition)

Mass analysis (m/z): 331 (M$^+$+1)

Nuclear magnetic resonance spectrum (DMSO-$d_6$, TMS internal standard):

δ: 4.77 (2H, s), 6.3–6.9 (1H, br), 7.07 (1H, s), 7.22–7.33 (2H, m), 7.36 (1H, s), 7.64 (1H, s), 7.80–7.87 (2H, m).

Example 7

A mixture of 465 mg of ethyl 2-[6-amino-2,3-dioxo-7-(1H-imidazol-1-yl)-1,2,3,4-tetrahydroquinoxalin-1-yl]acetate, 160 mg of formalin, 30 ml of water, 3 ml of 1N hydrochloric acid and 100 mg of 10% palladium-carbon was stirred in a hydrogen gas atmosphere for 8 hours, followed by filtration. The filtrate was concentrated under reduced pressure. The resulting residue was added to 4 ml of a 1N aqueous solution of sodium hydroxide at room temperature, followed by stirring for 1 hour. The reaction mixture was adjusted to about pH 6 with 1N hydrochloric acid. The crystals so precipitated were collected by filtration, washed with water, and dried under reduced pressure, followed by purification using a HP20 column to give 33 mg (6%) of 2-[2,3-dioxo-7-(1H-imidazol-1-yl)-6-methylamino-1,2,3,4-tetrahydroquinoxalin-1-yl]acetic acid•1 hydrochloride•1.45 hydrate.

Melting point: >300° C.

Mass analysis (m/z): 316 (M$^+$+1)

Nuclear magnetic resonance spectrum (DMSO-$d_6$, TMS internal standard):

δ: 2.65 (3H, s), 4.74 (2H, s), 5.58 (1H, br), 6.57 (1H, s), 7.51 (1H, s), 7.78 (1H, s), 7.84 (1H, s), 9.24 (1H, s), 12.18 (1H, s), 13.0–13.1 (1H, br).

Example 8

In a similar manner to Example 7 except for the use of 0.93 g of ethyl 2-[6-amino-2,3-dioxo-7-(1H-imidazol-1-yl)-

1,2,3,4-tetrahydroquinoxalin-1-yl]acetate, 0.92 g of formalin, 50 ml of water, 5 ml of 1N hydrochloric acid and 600 mg of 10% palladium-carbon, 395 mg (44%) of 2-[6-dimethylamino-2,3-dioxo-7-(1H-imidazol-1-yl)—,2,3,4-tetrahydroquinoxalin-1-yl]acetic acid•0.7 hydrate was obtained.

Melting point: >300° C.

Mass analysis (m/z): 329 (M$^+$)

Nuclear magnetic resonance spectrum (DMSO-d$_6$, TMS internal standard):

δ: 2.40 (6H, s), 4.87 (2H, s), 6.97 (1H, s), 7.10 (1H, s), 7.31 (1H, s), 7.42 (1H, s), 7.88 (1H, s), 12.14 (1H, s).

Example 9

To a mixture of 4.84 g (29 mmol) of glycine tert-butyl ester hydrochloride, 20 ml of THF, 4.1 ml of triethylamine and 3 ml of DMF, a mixture of 6.57 g of 2,4-difluoro-5-trifluoromethylnitrobenzene and 5 ml of THF was added dropwise under stirring. After stirring for 3 hours, 50 ml of ethyl acetate was added to the reaction mixture, followed by filtration. The filtrate was concentrated under reduced pressure. The concentrate was extracted by adding ethyl acetate and water. The organic layer was washed successively with water, a 1% aqueous solution of sodium bicarbonate and brine, dried over anhydrous sodium sulfate and then concentrated under reduced pressure. The residue was purified by chromatography on a silica gel column (eluting solvent: hexane:ethyl acetate=10:1.5) to give 9.54 g (98%) of N-(5-fluoro-2-nitro-4-trifluoromethylphenyl)glycine tert-butyl ester.

Nuclear magnetic resonance spectrum (CDCl$_3$, TMS internal standard):

δ: 1.54 (9H, s), 3.98 (2H, d, J=4.9 Hz), 6.46 (1H, d, J=12.7 Hz), 8.54 (1H, d, J=7.8 Hz), 8.76 (1H, bs).

2) A mixture of 9.36 g (27.7 mmol) of N-(5-fluoro-2-nitro-4-trifluoromethylphenyl)glycine tert-butyl ester, 7.54 g of imidazole and 30 ml of DMF was stirred for 2 hours on an oil bath at 60° C. After cooling, the reaction mixture was concentrated under reduced pressure. The residue was poured into water and the compound so precipitated was collected by filtration. The resulting compound was washed successively with water and ethyl ether and then dried under reduced pressure to give 8.95 g (84%) of N-[5-(1H-imidazol-1-yl)-2-nitro-4-trifluoromethylphenyl)glycine tert-butyl ester.

Nuclear magnetic resonance spectrum (CDCl$_3$, TMS internal standard):

δ: 1.52 (9H, s), 4.02 (2H, d, J=4.9 Hz), 6.67 (1H, s), 7.14 (1H, s), 7.21 (1H, s), 7.64 (1H, s), 8.66 (1H, s), 8.76 (1H, bs).

3) A mixture of 3.08 g (7.98 mmol) of N-[5-(1H-imidazol-1-yl)-2-nitro-4-trifluoromethylphenyl]glycine tert-butyl ester, 100 ml of THF, 50 ml of methanol and 350 mg of 10% palladium-carbon was stirred at normal pressure and room temperature under a hydrogen gas atmosphere. After the reaction, palladium-carbon was removed by filtration and the filtrate was concentrated under reduced pressure. To the resulting residue, 150 ml of chloroform and 2.46 ml of triethylamine were added. While stirring under ice cooling, a mixture of 2.29 g (16.7 mmol) of ethyl chloroglyoxylate and 20 ml of chloroform was added dropwise. After the dropwise addition, the reaction mixture was allowed to warm up to room temperature, followed by stirring overnight. Then, 200 ml of chloroform were added. The resulting mixture was washed successively with water and brine, dried over anhydrous sodium sulfate and concentrated under reduced pressure. The resulting residue was added with 100 ml of ethanol and 2 ml of 1N hydrochloric acid, followed by heating under reflux for 10 hours. After cooling, the reaction mixture was concentrated under reduced pressure. To the residue, 15 ml of trifluoroacetic acid was added, followed by stirring at room temperature for 6 hours. The reaction mixture was concentrated under reduced pressure, followed by the adjustment to pH 7 with a 1N aqueous solution of sodium hydroxide and a saturated aqueous solution of sodium bicarbonate. The resulting solution was purified using "HP-20" (a product of Mitsubishi Chemical Corporation; eluting solvent: water-methanol). The crude purified product so obtained was recrystallized from a 1N aqueous solution of hydrochloric acid to give 1.31 g (40%) of 2-[2,3-dioxo-7-(1H-imidazole-1-yl)-6-trifluoromethyl-1,2,3,4-tetrahydroquinoxalin-1-yl]acetic acid•1 hydrochloride•1 hydrate.

Melting point: 226–227° C.

Mass analysis (m/z): 354 (M$^+$)

Nuclear magnetic resonance spectrum (DMSO-d$_6$, TMS internal standard):

δ: 4.86 (1H, s), 7.89 (1H, s), 7.91 (1H, d, J=1.5 Hz), 8.04 (1H, s), 8.13 (1H, s), 9.54 (1H, s), 12.89 (1H, s), 12.5–14.0 (1H, bs).

In a similar manner to Example 9, the compounds of Examples 10 to 12 were obtained.

Example 10

1) By using 2.50 g of glycine tert-butyl ester hydrochloride, 20 ml of THF, 5 ml of DMF, 2.08 ml of triethylamine and 3.0 g of 2,4-difluoro-5-nitroacetophenone, 4.01 g (86%) of N-(4-acetyl-5-fluoro-2-nitrophenyl)glycine tert-butyl ester was obtained.

Nuclear magnetic resonance spectrum (CDCl$_3$, TMS internal standard):

δ: 1.53 (9H, s), 2.58 (3H, d, J=4.3 Hz), 3.98 (2H, d, J=4.9 Hz), 6.34 (1H, d, J=12.9 Hz), 8.90 (1H, d, J=8.2 Hz), 10.7 (1H, bs).

2) By using 3.77 g (12.1 mmol) of N-(4-acetyl-5-fluoro-2-nitrophenyl)glycine tert-butyl ester, 3.28 g of imidazole and 15 ml of DMF, 3.80 g (87%) of N-[4-acetyl-5-(1H-imidazol-1-yl)-2-nitrophenyl]glycine tert-butyl ester was obtained.

Nuclear magnetic resonance spectrum (CDCl$_3$, TMS internal standard):

δ: 1.53 (9H, s), 2.14 (3H, s), 4.02 (2H, d, J=5.1 Hz), 6.57 (1H, s), 7.09 (1H, S), 7.25 (1H, s), 7.63 (1H, s), 8.74 (1H, s), 8.76 (1H, bs).

3) N-[4-acetyl-5-(1H-imidazol-1-yl)-2-nitrophenyl] glycine tert-butyl ester (3.63 g), 120 ml of THF and 360 mg of 10% palladium-carbon were used and reduction was carried out. Then, by using 7.1 ml of triethylamine and 6.89 g of ethyl chloroglyoxylate, 1.32 g (37%) of 2-[6-acetyl-2,3-dioxo-7-(1H-imidazol-1-yl)-1,2,3,4-tetrahydroquinoxalin-1-yl]acetic acid•1 hydrate was obtained.

Melting point: 225–226° C. (decomposition) Nuclear magnetic resonance spectrum (DMSO-d$_6$, TMS internal standard):

δ: 2.40 (3H, s), 4.90 (2H, s), 7.73 (1H, s), 7.81 (1H, s), 7.84 (1H, s), 7.99 (1H, s), 9.16 (1H, s), 12.70 (1H, s), 12.9–14.3 (1H, bs).

Example 11

By using 5.60 g (21.4 mmol) of ethyl 2-(2,4-difluoro-5-nitrophenoxy)acetate, 3.59 g of glycine tert-butyl ester hydrochloride, 40 ml of THF, 10 ml of DMF and 3 ml of triethylamine, 2.27 g (28%) of 2-(4-tert-butoxycarbonylmethylamino-2-fluoro-5-nitrophenoxy) acetate was obtained.

Nuclear magnetic resonance spectrum (CDCl$_3$, TMS internal standard):

δ: 1.31 (3H, t, J=6.8 Hz), 1.52 (9H, s), 3.94 (2H, d, J=5.4 Hz), 4.28 (2H, q, J=6.8 Hz), 4.64 (2H, s), 6.45 (1H, d, J=12.7 Hz), 7.83 (1H, d, J=8.8 Hz), 8.42 (1H, s).

By using 2.13 g (5.73 mmol) of 2-(4-tert-butoxycarbonylmethylamino-2-fluoro-5-nitrophenoxy) acetate, 1.56 g of imidazole and 15 ml of DMF, 1.88 g (78%) of ethyl 2-[4-tert-butoxycarbonylmethylamino-$^2$-(1H-imidazol-1-yl)-5-nitrophenoxy]acetate was obtained.

Nuclear magnetic resonance spectrum (CDCl$_3$, TMS internal standard):

δ: 1.31 (3H, t, J=8.7 Hz), 1.52 (9H, s), 3.98 (2H, d, J=5.4 Hz), 4.27 (2H, q, J=8.7 Hz), 4.66 (2H, s), 6.65 (1H, s), 7.20 (1H, s), 7.39 (1H, s), 7.83 (1H, s), 8.01 (1H, s), 8.37 (1H, bs).

Ethyl 2-[4-tert-butoxycarbonylmethyl)amino-2-(1H-imidazol-1-yl)-5-nitrophenoxy]acetate (1.75 g, 4.71 mmol), 100 ml of THF and 0.3 g of 10% palladium-carbon were used and reduction was carried out. By using 3.3 ml of triethylamine and 3.22 g of ethyl chloroglyoxylate, 1.03 g (53%) of 2-[6-carboxymethoxy-2,3-dioxo-7-(1H-imidazol-1-yl)-1,2,3,4-tetrahydroquinoxalin-1-yl]acetic acid was obtained.

Melting point: >300° C. (decomposition)

Mass analysis (m/z): 360 (M$^+$)

Nuclear magnetic resonance spectrum (DMSO-d$_6$, TMS internal standard):

δ: 4.81 (2H, s), 4.88 (2H, s), 7.09 (1H, s), 7.81 (1H, s), 7.89 (1H, s), 8.02 (1H, s), 9.45 (1H, s), 12.40 (1H, s), 12.5–14.2 (1H, bs).

Example 12

1) By using 3.63 g of glycine tert-butyl ester hydrochloride, 25 ml of THF, 3.03 g of triethylamine, 5 ml of DMF and 5.0 g (21.6 mmol) of ethyl 2,4-difluoro-5-nitrobenzoate, 6.41 g (87%) of N-(4-ethoxycarbonyl-5-fluoro-2-nitrophenyl)glycine tert-butyl ester was obtained.

Nuclear magnetic resonance spectrum (CDCl$_3$, TMS internal standard):

δ: 1.39 (3H, t, J=8.3 Hz), 1.53 (9H, s), 3.98 (2H, d, J=4.9 Hz), 4.37 (2H, q, J=8.3 Hz), 6.36 (11H, d, J=12.7 Hz), 8.74 (1H, bs), 8.88 (1H, d, J=8.7 Hz).

2) By using 6.35 g (18.5 mmol) of N-(4-ethoxycarbonyl-5-fluoro-2-nitrophenyl)glycine tert-butyl ester, 5.05 g of imidazole and 20 ml of DMF, 7.01 g (97%) of N-[4-ethoxycarbonyl-5-(1H-imidazol-1-yl)-2-nitrophenyl] glycine tert-butyl was obtained.

Nuclear magnetic resonance spectrum (CDCl$_3$, TMS internal standard):

δ: 1.18 (3H, t, J=7.3 Hz), 1.52 (9H, s), 4.01 (2H, d, J=5.4 Hz), 4.19 (2H, q, J=7.3 Hz), 6.58 (1H, s), 7.07 (1H, s), 7.19 (1H, s), 7.60 (1H, s), 8.75 (1H, bs), 8.96 (1H, s).

3) A-mixture of 6.84 g (17.5 mmol) of N-[4-ethoxycarbonyl-5-(1H-imidazol-1-yl)-2-nitrophenyl] glycine tert-butyl ester, 150 ml of THF and 0.5 g of 10% palladium-carbon was stirred at room temperature and normal pressure under a hydrogen gas atmosphere. After the reaction, the catalyst was removed by filtration. To the filtrate, 12.3 ml of triethylamine were added. Under ice-cooling, a mixture of 11.96 g of ethyl chloroglyoxylate and 20 ml of THF was added dropwise with stirring. The reaction mixture was heated to room temperature, followed by stirring for 2 hours. The crystals so precipitated were removed by filtration and the filtrate was concentrated under reduced pressure. To the residue, 100 ml of ethanol was added, followed by heating under reflux for 3 hours. After cooling, the crystals so precipitated were collected by filtration, washed successively with ethanol and diethyl ether and then dried under reduced pressure. The resulting compound was added with 30 ml of trifluoroacetic acid and they were stirred at room temperature overnight. The reaction mixture was concentrated under reduced pressure. To the resulting residue, a 10N aqueous solution of sodium hydroxide and a 1N aqueous solution of sodium hydroxide were added to adjust the pH to 9 to 10, followed by stirring overnight. Concentrated hydrochloric acid and a 1N aqueous solution of hydrochloric acid were added to the reaction mixture to adjust the pH to 2 to 3. The crystals so precipitated were collected by filtration. The resulting compound was recrystallized from a 1N aqueous solution of hydrochloric acid to give 3.65 g (63%) of 2-[6-carboxy-2,3-dioxo-7-(1H-imidazol-1-yl)-1,2,3,4-tetrahydroquinoxalin-1-yl] acetic acid•0.15 hydrochloride•1.5 hydrate.

Melting point: >300° C.

Mass analysis (m/z): 330 (M$^+$)

Nuclear magnetic resonance spectrum (DMSO-d$_6$, TMS internal standard):

δ: 4.92 (2H, s), 7.18 (1H, s), 7.43 (1H, s), 7.56 (1H, s), 7.83 (1H, s), 8.08 (1H, s), 12.48 (1H, s).

Example 13

1) To a mixture of 6.86 g of 2,4-difluoro-5-anitrobenzonitrile, 22.67 g of triethylamine, 40 ml of DMF and 40 ml of THF, 5.20 g of glycine ethyl ester hydrochloride was added under ice-cooling, followed by stirring at the same temperature for 4 hours. To the reaction mixture, water was added and the reaction product was extracted with chloroform. The extract was washed successively with water and brine, dried over anhydrous sodium sulfate and then, concentrated under reduced pressure. The resulting residue was purified by chromatography on a silica gel column (eluent: hexane:ethyl acetate=80:20) to give 4.85 g (49%) of N-(4-cyano-5-fluoro-2-nitrophenyl)glycine ethyl ester.

Nuclear magnetic resonance spectrum (CDCl$_3$, TMS internal standard):

δ: 1.22–1.48 (3H, m), 4.08 (2H, d, J=5.3 Hz), 4.19–4.50 (2H, m), 6.46 (1H, d, J=11.3 Hz), 8.57 (1H, d, J=6.7 Hz), 8.80–9.05 (1H, br).

2) A mixture of 2.50 g of N-(4-cyano-5-fluoro-2-nitrophenyl)glycine ethyl ester, 0.67 g of imidazole, 7.40 g of pyridine and 40 ml of DMSO was stirred at 80° C. for 4 hours. After the addition of water, the reaction product was extracted with chloroform. The extract was washed successively with water and brine, dried over anhydrous sodium sulfate and then, concentrated under reduced pressure. The resulting residue was purified by chromatography on a silica gel column (eluent:chloroform:methanol=95:5) to give 2.82 g (92%) of N-[4-cyano-5-(1H-imidazol-1-yl)-2--nitrophenyl]glycine ethyl ester.

Nuclear magnetic resonance spectrum (DMSO-d$_6$, TMS internal standard):

δ: 1.15–1.26 (3H, m), 4.10–4.21 (2H, m), 4.45 (2H, d, J=5.5 Hz), 7.15–7.22 (2H, m), 7.68–7.73 (1H, m), 8.17 (1H, s), 8.75 (1H, s), 8.85–8.94 (1H, m).

3) A mixture of 2.00 g of N-[4-cyano-5-(1H-imidazol-1-yl)-2-nitrophenyl]glycine ethyl ester, 40 ml of THF, 8 ml of methanol and 200 mg of 10% palladium-carbon was stirred under a hydrogen gas atmosphere to reduce the nitro group. The reaction mixture was filtered and the filtrate was concentrated under reduced pressure. Then, 50 ml of chloroform and 4.43 ml of triethylamine were added to the resulting residue, followed by the dropwise addition of 1.69 ml of ethyl chloroglyoxylate under ice-cooling. After stirring at room temperature for 20 hours, the reaction mixture was diluted with chloroform. The diluted mixture was washed with brine, dried over anhydrous sodium sulfate and then concentrated under reduced pressure. Then, 60 ml of ethanol and 0.5 ml of concentrated hydrochloric acid were added to the resulting residue, followed by heating under reflux for 3 hours. After cooling, the crystals so formed were collected by filtration and dried under reduced pressure to give 1.07 g (50%) of ethyl 2-[6-cyano-2,3-dioxo-7-(1H-imidazol-1-yl)-1,2,3,4-tetrahydroquinoxalin-1-yl]acetate.

Nuclear magnetic resonance spectrum (DMSO-$d_6$, TMS internal standard):

$\delta$: 1.15–1.25 (3H, m), 4.10–4.20 (2H, m), 4.99 (2H, s), 7.84 (1H, s), 7.90 (1H, s), 8.04 (1H, s), 8.16 (1H, s), 9.47 (1H, s), 12.83 (1H, s).

4) To 6 ml of a 1N aqueous solution of sodium hydroxide, 672 mg of ethyl 2-[6-cyano-2,3-dioxo-7-(1H-imidazol-1-yl)-1,2,3,4-tetrahydroquinoxalin-1-yl]acetate was added at room temperature, followed by stirring for one hour to hydrolyze the ester. The reaction mixture was adjusted to about pH 1 with 1N hydrochloric acid. The crystals so precipitated were collected by filtration, washed with water and then dried under reduced pressure to give 417 mg (62%) of 2-[6-cyano- 2,3-dioxo-7-(1H-imidazol-1-yl)-1,2,3,4-tetrahydroquinoxalin-1-yl]acetic acid•1.7 hydrate.

Melting point: 283–285° C. (decomposition)

Nuclear magnetic resonance spectrum (DMSO-$d_6$, TMS internal standard):

$\delta$: 4.95 (2H, s), 7.17 (1H, s), 7.62 (2H, s), 7.74 (1H, s), 8.06 (1H, s), 12.54 (1H, s), 13.2–13.4 (1H, br).

In a similar manner to Example 13, the compounds of Examples 14 to 20 were obtained.

Example 14

1) By using 3.00 g of 2,4-difluoro-5-nitrotoluene, 8.77 g of triethylamine, 40 ml of DMF, 40 ml of THF and 2.42 g of glycine ethyl ester hydrochloride, 2.70 g (61%) of N-(5-fluoro-4-methyl-2-nitrophenyl)glycine ethyl ester was obtained.

Nuclear magnetic resonance spectrum (CDCl$_3$, TMS internal standard):

$\delta$: 1.29–1.36 (3H, m), 2.20 (3H, s), 4.03 (2H, d, J=5.5 Hz), 4.24–4.34 (2H, m), 6.32 (1H, d, J=11.6 Hz), 8.10 (1H, d, J=7.9 Hz), 8.39 (1H, br).

2) By using 1.00 g of N-(5-fluoro-4-methyl-2-nitrophenyl)glycine ethyl ester, 266 mg of imidazole and 10 ml of pyridine, 470 mg (39%) of N-[5-(1H-imidazol-1-yl)-4-methyl-2-nitrophenyl]glycine ethyl ester was obtained.

Nuclear magnetic resonance spectrum (CDCl$_3$, TMS internal standard):

$\delta$: 1.26–1.36 (3H, m), 2.15 (3H, s), 4.05 (2H, d, J=5.5 Hz), 4.23–4.33 (2H, m), 6.55 (1H, s), 7.09 (1H, s), 7.24 (1H, s), 7.63 (1H, s), 8.20 (1H, s), 8.32 (1H, br).

3) By using 467 mg of N-[5-(1H-imidazol-1-yl)-4-methyl-2-nitrophenyl]glycine ethyl ester, 221 mg (44%) of ethyl 2-[2,3-dioxo-7-(1H-imidazol-1-yl)-6-methyl-1,2,3,4-tetrahydroquinoxalin-1-yl]acetate was obtained.

Nuclear magnetic resonance spectrum (DMSO-$d_6$, TMS internal standard):

$\delta$: 1.21 (3H, t, J=7.3 Hz), 2.17 (3H, s), 4.10–4.19 (2H, m), 7.25 (1H, s), 7.70 (1H, s), 7.89 (1H, s), 7.98 (1H, s), 12.45 (1H, s).

4) By using 218 mg of ethyl 2-[2,3-dioxo-7-(1H-imidazol-1-yl)-6-methyl-1,2,3,4-tetrahydroquinoxalin-1-yl]acetate, 180 mg (79%) of 2-[2,3-dioxo-7-(1H-imidazol-1-yl)-6-methyl-1,2,3,4-tetrahydroquinoxalin-1-yl]acetic acid•1 hydrochloride•0.4 hydrate was obtained.

Melting point: >300° C.

Mass analysis (m/z): 301 (M$^+$+1)

Nuclear magnetic resonance spectrum (DMSO-$d_6$, TMS internal standard):

$\delta$: 2.17 (3H, s), 4.83 (2H, s), 7.25 (1H, s), 7.72 (1H, s), 7.90 (1H, s), 7.99 (1H, s), 9.34 (1H, s), 12.46 (1H, s), 13.1–13.3 (1H, br).

Example 15

1) By using 2.00 g of 2,4,5-trifluoronitrobenzene, 3.43 g of triethylamine, 25 ml of DMF, 25 ml of THF and 1.58 g of glycine ethyl ester hydrochloride, 0.59 g (20%) of N-(4,5-difluoro-2-nitrophenyl)glycine ethyl ester was obtained.

Nuclear magnetic resonance spectrum (CDCl$_3$, TMS internal standard):

$\delta$: 1.20–1.45 (3H, m), 4.03 (2H, d, J=5.3 Hz), 4.15–4.47 (2H, m), 6.48 (1H, dd, J=12.2, 6.6 Hz), 8.10 (1H, dd, J=10.6, 8.4 Hz), 8.3–8.6 (1H, br).

2) By using 0.59 g of N-(4,5-difluoro-2-nitrophenyl)glycine ethyl ester, 155 mg of imidazole, 1.80 g of pyridine and 10 ml of DMSO, 0.41 g (59%) of N-[4-fluoro-5-(1H-imidazol-1-yl)-2-nitrophenyl]glycine ethyl ester was obtained.

Nuclear magnetic resonance spectrum (CDCl$_3$, TMS internal standard):

$\delta$: 1.20–1.46 (3H, m), 4.03–4.48 (4H, m), 6.66 (1H, d, J=6.1 Hz), 7.20–7.40 (2H, m), 7.90 (1H, br), 8.10–8.60 (2H, m).

3) By using 406 mg of N-[4-fluoro-5-(1H-imidazol-1-yl)-2-nitrophenyl]glycine ethyl ester, 154 mg (35%) of ethyl 2-[2,3-dioxo-6-fluoro-7-(1H-imidazol-1-yl)-1,2,3,4-tetrahydroquinoxalin-1-yl]acetate was obtained.

Nuclear magnetic resonance spectrum (DMSO-$d_6$, TMS internal standard):

$\delta$: 1.16–1.29 (3H, m), 4.12–4.22 (2H, m), 4.98 (2H, s), 7.33 (1H, d, J=10.8 Hz), 7.81–7.96 (2H, m), 8.06 (1H, s), 9.36 (1H, s), 12.58 (1 H, s).

4) By using 152 mg of ethyl 2-[2,3-dioxo-6-fluoro-7-(1H-imidazol-1-yl)-1,2,3,4-tetrahydroquinoxalin-1-yl]acetate, 90 mg (61%) of 2-[2,3-dioxo-6-fluoro-7-(1H-imidazol-1-yl)-1,2,3,4-tetrahydroquinoxalin-1-yl]acetic acid•1 hydrate was obtained.

Melting point: >300° C.

Mass analysis (m/z): 305 (M$^+$+1)

Nuclear magnetic resonance spectrum (DMSO-$d_6$, TMS internal standard):

$\delta$: 4.93 (2H, s), 7.13 (1H, s), 7.21 (1H, d, J=10.4 Hz), 7.55 (1H, s), 7.65 (1H, d, J=6.7 Hz), 8.01 (1H, s), 12.36 (1H, s), 13.0–13.2 (1H, br).

Example 16

1) By using 6.32 g of 5-chloro-2,4-difluoronitrobenzene, 9.91 g of triethylamine, 60 ml of DMF, 60 ml of THF and 4.56 g of glycine ethyl ester hydrochloride, 0.66 g (7%) of N-(4-chloro-5-fluoro-2-nitrophenyl)glycine ethyl ester was obtained.

Nuclear magnetic resonance spectrum (CDCl$_3$, TMS internal standard):

$\delta$: 1.16–1.47 (3H, m), 4.04 (2H, d, J=5.3 Hz) 4.16–4.45 (2H, m), 6.47 (1H, d, J=11.1 Hz), 8.25–8.67 (2H, m).

2) By using 0.66 g of N-(4-chloro-5-fluoro-2-nitrophenyl)glycine ethyl ester, 162 mg of imidazole and 4 ml of pyridine, 0.44 g (57%) of N-[4-chloro-5-(1H-imidazol-1-yl)-2-nitrophenyl]glycine ethyl ester was obtained.

Nuclear magnetic resonance spectrum ($CDCl_3$, TMS internal standard):

δ: 1.16–1.44 (3H, m), 4.07 (2H, d, J=5.2 Hz), 4.16–4.48 (2H, m), 6.65 (1H, s), 7.15–7.37 (2H, m), 7.76 (1H, s), 8.35–8.63 (2H, m).

3) By using 442 mg of N-[4-chloro-5-(1H-imidazol-1-yl)-2-nitrophenyl]glycine ethyl ester, 235 mg (50%) of ethyl 2-[6-chloro-2,3-dioxo-7-(1H-imidazol-1-yl)-1,2,3,4-tetrahydroquinoxalin-1-yl]acetate was obtained.

Nuclear magnetic resonance spectrum (DMSO-$d_6$, TMS internal standard):

δ: 1.17–1.24 (3H, m), 4.12–4.20 (2H, m), 4.93 (2H, s), 7.48 (1H, s), 7.81 (1H, s), 7.91–7.98 (2H, m), 9.23 (1H, s), 12.54 (1H, s).

4) By using 225 mg of ethyl 2-[6-chloro-2,3-dioxo-7-(1H-imidazol-1-yl)-1,2,3,4-tetrahydroquinoxalin-1-yl]acetate, 163 mg (79%) of 2-[6-chloro-2,3-dioxo-7-(1H-imidazol-1-yl)- 1,2,3,4-tetrahydroquinoxalin-1-yl]acetic acid•0.7 hydrate was obtained.

Melting point: 295–298° C.

Mass analysis (m/z): 321 ($M^+$+1)

Nuclear magnetic resonance spectrum (DMSO-$d_6$, TMS internal standard):

δ: 4.90 (2H, s), 7.15 (1H, s), 7.37–7.47 (2H, m), 7.67 (1H, s), 7.92 (1H, s), 12.40 (1H, s).

Example 17

1) By using 7.61 g (54.5 mmol) of glycine ethyl ester hydrochloride, 15 ml of THF, 7.64 ml of triethylamine, 10 ml of DMF and 11.8 g (49.6 mmol) of 5-bromo-2,4-difluoronitrobenzene, 10.5 g (60%) of N-(4-bromo-5-fluoro-2-nitrophenyl)glycine ethyl ester was obtained.

Nuclear magnetic resonance spectrum ($CDCl_3$, TMS internal standard):

δ: 1.33 (3H, t, J=7.4 Hz), 4.04 (2H, d, J=4.9 Hz), 4.30 (2H, q, J=7.4 Hz), 6.46 (1H, d, J=10.9 Hz), 8.44 (1H, d, J=7.3 Hz), 8.49 (1H, bs). 2) By using 3.36 g (10.5 mmol) of N-(4-bromo-5-fluoro-2-nitrophenyl)glycine ethyl ester, 2.86 g of imidazole and 20 ml of DMF, 3.50 g (90%) of N-[4-bromo-5-(1H-imidazol-1-yl)-2-nitrophenyl]glycine ethyl ester was obtained.

Nuclear magnetic resonance spectrum ($CDCl_3$, TMS internal standard):

δ: 1.32 (3H, t, J=7.4 Hz), 4.05 (2H, dd, J=5.2, 14.9 Hz), 4.29 (2H, q, J=7.4 Hz), 6.64 (1H, d, J=9.1 Hz), 7.19 (1H, s), 7.23 (1H, s), 7.72 (1H, s), 7.72 (1H, s), 8.45 (1H, bs), 8.57 (1H, s).

3) A mixture of 3.24 g (8.78 mmol) of N-[4-bromo-5-(1H-imidazol-1-yl)-2-nitrophenyl]glycine ethyl ester, 70 ml of THF, 50 ml of methanol and about 0.5 g of Raney nickel was stirred at room temperature and normal pressure under a hydrogen gas atmosphere. After the reaction, the catalyst was removed by filtration and the filtrate was concentrated under reduced pressure. To the residue, 100 ml of chloroform and 3.1 ml of triethylamine were added. Under ice-cooling, a mixture of 3.02 g of ethyl chloroglyoxylate and 20 ml of chloroform was added dropwise to the resulting mixture under stirring. The reaction mixture was heated to room temperature, followed by stirring overnight. The reaction mixture was diluted with 150 ml of chloroform, washed successively with water, a 5% aqueous solution of sodium bicarbonate and brine, dried over anhydrous sodium sulfate and then concentrated under reduced pressure. Then, 100 ml of ethanol and 1.5 ml of concentrated hydrochloric acid were added, followed by heating under reflux for 6 hours.

After cooling, the reaction mixture was concentrated under reduced pressure. Then, 15 ml of a 1N aqueous solution of sodium hydroxide was added, followed by stirring for 2 hours. To the reaction mixture, a 1N aqueous solution of hydrochloric acid was added to adjust the pH to 2 to 3 and the compound so precipitated was collected by filtration. The resulting compound was recrystallized from a 1N aqueous solution of hydrochloric acid to give 2.02 g (55%) of 2-[6-bromo-2,3-dioxo-7-(1H-imidazol-1-yl)-1,2,3,4-tetrahydroquinoxalin-1-yl]acetic acid•1 hydrochloride•0.8 hydrate.

Melting point: 283° C. (decomposition)

Mass analysis (m/z): 365, 367 ($M^+$)

Nuclear magnetic resonance spectrum (DMSO-$d_6$, TMS internal standard):

δ: 4.84 (2H, s), 7.75 (1H, s), 7.93 (1H, s), 8.02 (1H, s), 8.03 (1H, s), 9.48 (1H, s), 12.75 (1H, s), 12.6–14.0 (1H, b).

Example 18

1) By using 2.78 g of 2,4-difluoro-5-nitrophenylmethyl ether, 4.45 g of triethylamine, 30 ml of DMF, 30 ml of THF and 2.05 g of glycine ethyl ester, 0.52 g (13%) of N-(5-fluoro-4-methoxy-2-nitrophenyl)glycine ethyl ester was obtained.

Nuclear magnetic resonance spectrum ($CDCl_3$, TMS internal standard):

δ: 1.19–1.45 (3H, m), 3.80–4.46 (7H, m), 6.45 (1H, d, J=13.1 Hz), 7.81 (1H, d, J=8.8 Hz), 8.3–8.6 (1H, br).

2) By using 420 mg of N-(5-fluoro-4-methoxy-2-nitrophenyl)glycine ethyl ester, 420 mg of imidazole and 2.5 ml of DMF, 200 mg (41%) of N-[5-(1H-imidazol-1-yl)-4-methoxy-2-nitrophenyl]glycine ethyl ester was obtained.

Nuclear magnetic resonance spectrum ($CDCl_3$, TMS internal standard):

δ: 1.27–1.37 (3H, m), 3.88 (3H, s), 4.09 (2H, d, J=5.5 Hz), 4.25–4.34 (2H, m), 6.64 (1H, s), 7.20 (1H, s), 7.27 (1H, s), 7.85–7.94 (2H, m), 8.32–8.40 (1H, m).

3) By using 196 mg of N-[5-(1H-imidazol-1-yl)-4-methoxy-2-nitrophenyl]glycine ethyl ester, 46 mg (22%) of ethyl 2-[2,3-dioxo-7-(1H-imidazol-1-yl)-6-methoxy-1,2,3,4-tetrahydroquinoxalin-1-yl]acetate was obtained.

Nuclear magnetic resonance spectrum (DMSO-$d_6$, TMS internal standard):

δ: 1.17–1.25 (3H, m), 3.85 (3H, s), 4.11–4.20 (2H, m), 4.94 (2H, s), 7.09 (1H, s), 7.75 (1H, s), 7.79 (1H, s), 7.92 (1H, s), 9.24 (1H, s), 12.37 (1H, s).

4) By using 44 mg of ethyl 2-[2,3-dioxo-7-(1H-imidazol-1-yl)-6-methoxy-1,2,3,4-tetrahydroquinoxalin-1-yl]acetate, 33 mg (7.5%) of 2-[2,3-dioxo-7-(1H-imidazol-1-yl)-6-methoxy-1,2,3,4-tetrahydroquinoxalin-1-yl]acetic acid•0.1 hydrochloride•1.5 hydrate was obtained.

Melting point: >300° C.

Mass analysis (m/z): 317 ($M^+$+1)

Nuclear magnetic resonance spectrum (DMSO-$d_6$, TMS internal standard):

δ: 3.81 (3H, s), 4.91 (2H, s), 7.02 (1H, s), 7.12 (1H, s), 7.43–7.51 (2H, m), 7.99 (1H, s), 12.23 (1H, s), 13.0–13.3 (1H, br).

Example 19

1) By using 4.41 g of benzyl 2,4-difluoro-5-nitrophenyl ether, 5.05 g of triethylamine, 30 ml of DMF, 30 ml of THF and 2.32 g of glycine ethyl ester hydrochloride, 454 mg (8%) of N-(4-benzyloxy-5-fluoro-2-nitrophenyl)glycine ethyl ester was obtained.

Nuclear magnetic resonance spectrum (CDCl$_3$, TMS internal standard):

δ: 1.32 (3H, t, J=7.3 Hz), 4.03 (2H, d, J=5.5 Hz), 4.25–4.33 (2H, m), 5.09 (2H, s), 6.44 (1H, d, J=12.2 Hz), 7.30–7.48 (5H, m), 7.99 (1H, d, J=8.5 Hz), 8.40 (1H, br).

2) By using 448 mg of N-(4-benzyloxy-5-fluoro-2-nitrophenyl)glycine ethyl ester, 350 mg of imidazole and 2 ml of DMF, 331 mg (65%) of N-[4-benzyloxy-5-(1H-imidazol-1-yl)-2-nitrophenyl]glycine ethyl ester was obtained.

Nuclear magnetic resonance spectrum (CDCl$_3$, TMS internal standard):

δ: 1.32 (3H, t, J=7.3 Hz), 4.08 (2H, d, J=5.5 Hz), 4.25–4.34 (2H, m), 5.09 (2H, S), 6.63 (1H, s), 7.20 (1H, s), 7.25–7.40 (6H, m), 7.92 (1H, s), 8.00 (1H, s), 8.31–8.37 (1H, m).

3) By using 100 mg of N-[4-benzyloxy-5-(1H-imidazol-1-yl)-2-nitrophenyl]glycine ethyl ester, 70 mg (66%) of ethyl 2-[6-benzyloxy-2,3-dioxo-7-(1H-imidazol-1-yl)-1,2,3,4-tetrahydroquinoxalin-1-yl]acetate was obtained.

Nuclear magnetic resonance spectrum (DMSO-d$_6$, TMS internal standard):

δ: 1.08–1.33 (3H, m), 4.16 (2H, q, J=7.3 Hz), 4.95 (2H, s), 5.19 (2H, s), 7.15–7.52 (6H, m), 7.75–7.92 (2H, m), 7.94–8.08 (1H, m), 9.36–9.48 (1H, m), 12.47 (1H, s).

4) By using 134 mg of ethyl 2-[6-benzyloxy-2,3-dioxo-7-(1H-imidazol-1-yl)-1,2,3,4-tetrahydroquinoxalin-1-yl]acetate, 86 mg (62%) of 2-[6-benzyloxy-2,3-dioxo-7-(1H-imidazol-1-yl)-1,2,3,4-tetrahydroquinoxalin-1-yl]acetic acid•0.5 hydrochloride•1.4 hydrate was obtained.

Melting point: 275° C. (decomposition)

Mass analysis (m/z): 393 (M$^+$+1)

Nuclear magnetic resonance spectrum (DMSO-d$_6$, TMS internal standard):

δ: 4.88 (2H, s), 5.17 (2H, s), 7.13 (1H, s), 7.30–7.48 (6H, m), 7.64 (1H, s), 7.74 (1H, s), 8.66 (1H, s), 12.32 (1H, s).

Example 20

1) By using 1.82 g of 2,4-difluoro-5-nitrophenylmethylsulfone, 0.78 g of triethylamine, 4 ml of DMF, 8 ml of THF and 1.07 g of glycine ethyl ester hydrochloride, 2.44 g (99%) of N-(5-fluoro-4-methylsulfonyl-2-nitrophenyl)glycine ethyl ester was obtained.

Nuclear magnetic resonance spectrum (CDCl$_3$, TMS internal standard):

δ: 1.15–1.55 (3H, m), 3.19 (3H, s), 3.93–4.50 (4H, m), 6.49 (1H, d, J=12.0 Hz), 8.76–9.07 (2H, m). 2) By using 1.00 g of N-(5-fluoro-4-methylsulfonyl-2-nitrophenyl)glycine ethyl ester, 0.85 g of imidazole and 5 ml of DMF, 0.35 g (67%) of N-[5-(1H-imidazol-1-yl)-4-methylsulfonyl-2-nitrophenyl]glycine ethyl ester was obtained.

Nuclear magnetic resonance spectrum (DMSO-d$_6$, TMS internal standard):

δ: 1.08–1.32 (3H, m), 2.86 (3H, s), 4.16 (2H, q, J=7.3 Hz), 4.41 (2H, d, J=6.0 Hz), 7.09–7.23 (2H, m), 7.43–7.51 (1H, m), 7.83–7.90 (1H, m), 8.72 (1H, s), 8.80–9.03 (1H, m).

3) By using 345 mg of N-[5-(1H-imidazol-1-yl)-4-methylsulfonyl-2-nitrophenyl]glycine ethyl ester, 265 mg (72%) of ethyl 2-[2,3-dioxo-7-(1H-imidazol-1-yl)-6-methylsulfonyl-1,2,3,4-tetrahydroquinoxalin-1-yl]acetate was obtained.

Nuclear magnetic resonance spectrum (DMSO-d$_6$, TMS internal standard):

δ: 1.16–1.25 (3H, m), 3.18 (3H, s), 4.12–4.20 (2H, m), 4.95 (2H, s), 7.83 (1H, s), 7.94–8.06 (3H, m), 9.37 (1H, s), 12.75 (1H, s).

4) By using 150 mg of ethyl 2-[2,i-dioxo-7-(1H-imidazol-1-yl)-6-methylsulfonyl-1,2,3,4-tetrahydroquinoxalin-1-yl]acetate, 106 mg (68%) of 2-[2,3-dioxo-7-(1H-imidazol-1-yl)-6-methylsulfonyl-1,2,3,4-tetrahydroquinoxalin-1-yl]acetic acid•0.6 hydrochloride•1.2 hydrate was obtained.

Melting point: >300° C.

Mass analysis (m/z): 365 (M$^+$+1)

Nuclear magnetic resonance spectrum (DMSO-d$_6$, TMS internal standard):

δ: 3.06 (3H, s), 4.88 (2H, s), 7.59 (1H, s), 7.82 (11H, s), 7.88–7.98 (2H, m), 8.84 (1H, s), 12.68 (1H, s), 13.1–13.5 (1H, br).

Example 21

A mixture of 1.63 g of ethyl 2-[2,3-dioxo-7-fluoro-6-nitro-1,2,3,4-tetrahydroquinoxalin-1-yl]acetate, 4 ml of a 50% aqueous solution of dimethylamine and 10 ml of DMF was heated and stirred on an oil bath of 10° C. under an argon gas atmosphere for 5 hours. After cooling, the reaction mixture was concentrated under reduced pressure. To the residue, 15 ml of a 1N aqueous solution of sodium hydroxide were added, followed by stirring at 30° C. for 3 hours. The reaction mixture was concentrated to half of the original amount under reduced pressure, followed by the addition of 3N hydrochloric acid to adjust the pH of the resulting mixture to 5 to 6. The crystals so precipitated were collected by filtration, washed with 1N hydrochloric acid and dried under reduced pressure. The resulting crude crystals were recrystallized from 1N hydrochloric acid to give 742 mg (45%) of 2-[7-dimethylamino-6-nitro-1,2,3,4-tetrahydroquinoxalin-1-yl]acetic acid•0.5 hydrate.

Melting point: >300° C.

Mass analysis (m/z): 309 (M$^+$+1)

Nuclear magnetic resonance spectrum (DMSO-d$_6$, TMS internal standard):

δ: 2.82 (6H, s), 4.97 (2H, s), 6.83 (1H, s), 7.45 (1H, s), 12.17 (1H, bs).

Example 22

A mixture of 2.94 g of ethyl 2-[7-fluoro-2,3-dioxo-6-nitro-1,2,3,4-tetrahydroquinoxalin-1-yl]acetate, 1.36 g of imidazole and 20 ml of DMF was stirred under heating at 120° C. for 3 hours. After cooling, the reaction mixture was poured into ice water. The crystals so precipitated were collected by filtration, washed with water and dried under reduced pressure to give 3.45 g (99%) of ethyl 2-[2,3-dioxo-7-(1H-imidazol-1-yl)-6-nitro-1,2,3,4-tetrahydroquinoxalin-1-yl]acetate•0.65 hydrate.

Melting point: 159–160° C. (decomposition)

Mass-analysis (m/z): 359 (M$^+$)

Nuclear magnetic resonance spectrum (DMSO-d$_6$, TMS internal standard):

δ: 1.21 (3H, t, J=7.1 Hz), 4.16 (2H, q, J=7.1 Hz), 5.03 (2H, s), 7.09 (1H, s), 7.39 (1H, s), 7.75 (1H, s), 7.87 (1H, s), 8.00 (1H, s), 12.60 (1H, bs).

Example 23

1) A mixture of 5.85 g (20 mmol) of 2-[5-(1H-imidazol-1-yl)-2-nitrophenyl]acetate, 250 ml of THF and 1.5 g of 10% palladium-carbon was stirred at room temperature under a hydrogen gas atmosphere. After the reduction of the nitro group, the catalyst was removed by filtration. To the filtrate, 11.3 ml of triethylamine was added. Under ice-cooling, a mixture of 11 g of ethyl chloroglyoxylate and 30 ml of THF was added dropwise to the resulting mixture, followed by stirring. After the dropwise addition, the reaction mixture was heated to room temperature and stirred overnight. The insoluble matter so formed was removed by filtration. The filtrate was concentrated under reduced pressure. To the residue, 150 ml of ethanol was added, followed by heating under reflux for 5 hours under an argon gas atmosphere. After cooling, the precipitate so formed was collected by filtration, washed with ethanol and dried under reduced pressure to give 3.94 g (60%) of ethyl 2-[2,3-dioxo-7-(1H-imidazol-1-yl)-1,2,3,4-tetrahydroquinoxalin-1-yl]acetate.

Mass-analysis (m/z): 314 (M$^+$)

Nuclear magnetic resonance spectrum (DMSO-d$_6$, TMS internal standard):

δ: 1.22 (3H, t, J=7.0 Hz), 4.18 (2H, q, J=7.0 Hz), 5.06 (2H, s), 7.41 (1H, d, J=8.6 Hz), 7.60 (1H, d-d, J=2.5, 8.6 Hz), 7.65 (1H, s), 7.77 (1H, d, J=25 Hz), 8.13 (1H, s),. 9.24 (1H, s), 12.47 (1H, s)

2) At the temperature of 0C or less, 3.63 g of ethyl 2-[2,3-dioxo-7-(1H-imidazol-1-yl)-1,2,3,4-tetrahydroquinoxalin-1-yl]acetate was dissolved in 15 ml of fuming nitric acid under stirring. The resulting solution was heated to room temperature, stirred for one hour, and poured into ice water, followed by adjustment to about pH 2.0 with an aqueous solution of sodium hydroxide. The resulting insoluble matter was removed by filtration. To the filtrate, an aqueous solution of sodium hydroxide was added to adjust the pH of the resulting liquid to about pH 6.5. The resulting insoluble matter was collected by filtration, washed with water and dried under reduced pressure to give 1.07 g (26%, purity: about 95% (HPLC)) of ethyl 2-[2,3-dioxo-7-(1H-imidazol-1-yl)-6-nitro-1,2,3,4-tetrahydroquinoxalin-1-yl] acetate.

3) A mixture of 2.12 g of ethyl 2-[2,3-dioxo-7-(1H-imidazol-1-yl)-6-nitro-1,2,3,4-tetrahydroquinoxalin-1-yl] acetate and 13 ml of a 1N aqueous solution of sodium hydroxide-was stirred at room temperature under an argon gas atmosphere. After the reaction, 0.5 ml of concentrated hydrochloric acid and a proper amount of 1N hydrochloric acid were added to the reaction mixture to adjust the pH to about 3.0. The crystals so precipitated were collected by filtration, washed with 1N hydrochloric acid and dried under reduced pressure. The resulting crude crystals were recrystallized from 1N hydrochloric acid to give 1.90 g (84%) of 2-[2,3-dioxo-7-(1H-imidazol-1-yl)-6-nitro-1,2,3,4-tetrahydroquinoxalin-1-yl]acetic acid•1 hydrochloride•1 hydrate.

Melting point: 248–250° C. (decomposition)

Mass analysis (m/z): 331 (M$^+$)

Nuclear magnetic resonance spectrum (DMSO-d$_6$, TMS internal standard):

δ: 4.90 (2H, s), 7.89 (1H, s), 8.03 (1H, s), 8.09 (1H, s), 8.33 (1H, s), 9.48 (1H, s), 12.96 (1H, s).

Example 24

To 66 ml of a 1N aqueous solution of sodium hydroxide, 8.5 g of the compound of Example 23 was added gradually under ice-cooling to dissolve the latter in the former. To the resulting solution, 44 ml of a 1N aqueous solution of hydrochloric acid was added gradually under ice-cooling.

The crystals so precipitated were collected by filtration and dried to give 6.8 g of 2-[2,3-dioxo-7-(1H-imidazol-1-yl)-6-nitro-1,2,3,4-tetrahydroquinoxalin-1-yl]acetic acid in the form of 6.8 g crystals.

|  | C(%) | H(%) | N(%) |
|---|---|---|---|
| Calculated: | 46.63 | 2.83 | 20.92 |
| Found: | 46.51 | 2.91 | 21.00 |

Nuclear magnetic resonance spectrum (DMSO-d$_6$, TMS internal standard):

δ: 4.95 (2H, s), 7.10 (1H, s), 7.40 (1H, s), 7.73 (1H, s), 7.88 (1H, s), 8.00 (1H, s), 12.58 (1H, s), 13.4 (1H, brs).

Example 25

1) To a mixture of 5.06 g (32.9 mmol) of 2,4-difluoronitrobenzene, 5.24 g of 5-aminovaleric acid hydrochloric acid and 20 ml of THF, 9.24 ml of triethylamine was added, followed by heating under reflux for 18 hours. After cooling, the reaction mixture was diluted with ethyl acetate and insoluble matter was removed by filtration. The filtrate was concentrated under reduced pressure. The resulting residue was recrystallized from ethyl acetate-ethyl ether to give 4.73 g (56%) of 6-(3-fluoro-6-nitrophenyl) aminovaleric acid.

Mass analysis (m/z): 256 (M$^+$)

Nuclear magnetic resonance spectrum (DMSO-d$_6$, TMS internal standard):

δ: 1.78–1.83 (4H, m), 2.44–2.48 (2H, rn), 3.29 (2H, q, J=7.0 Hz), 3.34–3.39 (1H, m), 6.45–6.49 (1H, m), 8.16–8.23 (1H, m).

2) A mixture of 2.19 g (8.55 mmol) of 5-(3-fluoro-6-nitrophenyl)aminovaleric acid, 100 ml of 2-propanol and 5 ml of 4N hydrochloric acid-dioxane was subjected to heating under reflux for 2 hours. After cooling, the reaction mixture was concentrated under reduced pressure. The residue was purified by chromatography on a silica gel column (developing solvent: hexane:ethyl acetate=9:1 to 6:1) to give 2.55 g (stoichiometric) of isopropyl 5-(3-fluoro-6-nitrophenyl)aminovalerate.

Mass analysis (m/z): 298 (M$^+$)

Nuclear magnetic resonance spectrum (CDCl$_3$, TMS internal standard):

δ: 1.24 (6H, d, J=6.4 Hz), 1.76–2.82 (4H, mn), 2.36 (2H, t, J=6.8 Hz), 3.28 (2H, d, J=5.4 Hz), 5.03 (1H, q, J=6.4 Hz), 6.33–6.39 (1H, m), 6.47 (1H, dd, J=2.5, 11.7 Hz), 8.17–8.23 (1H, m).

3) A mixture of 2.53 g (8.48 mmol) of isopropyl 5-(3-fluoro-6-nitrophenyl)aminovalerate, 100 ml of THF and 380 mg of 10% palladium-carbon was stirred at room temperature and normal pressure for 5 hours under a hydrogen gas atmosphere. After the reaction, the catalyst was removed by filtration. To the filtrate, 5.94 ml of triethylamine was added, followed by ice-cooling under an argon gas atmosphere. To the resulting solution, a mixture of 5.49 g of ethyl chloroglyoxylate and 15 ml of THF was added dropwise under stirring. After stirring for 1 hour, insoluble matter was removed by filtration and the filtrate was concentrated under reduced pressure. To the resulting residue, 150 ml of ethanol was added, followed by heating-under reflux for 18 hours. After cooling, the reaction mixture was concentrated to the one-third of the original volume under reduced pressure. To the resulting residue, 100 ml of ethyl ether were added. The insoluble matter so precipitated was collected by filtration and dried under reduced pressure to give 2.17 g (79%) of isopropyl 5-[2,3-dioxo-7-fluoro-1,2,3,4-tetrahydroquinoxalin-1-yl]valerate.

Mass analysis (m/z): 322 (M⁺)

Nuclear magnetic resonance spectrum (DMSO-$d_6$, TMS internal standard):

δ: 1.16 (6H, d, J=6.1 Hz), 1.60–1.62 (4H, m), 2.32 (2H, t, J=6.7 Hz), 4.01–4.08 (2H, m), 4.87 (1H, q, J=6.1 Hz), 7.01–7.05 (1H, m), 7.18 (1H, dd, J=5.5, 8.6 Hz), 7.32 (1H, dd, J=2.7, 11 Hz), 12.0 (1H, s). 4) In 10 ml of concentrated sulfuric acid cooled on an ice-methanol bath, 1.96 g (6.07 mmol) of isopropyl 5-[2,3-dioxo-7-fluoro-1,2,3,4-tetrahydroquinoxalin-1-yl]valerate was dissolved under stirring. To the resulting mixture, 300 μl of fuming nitric acid was added dropwise at –5° C. or lower, followed by stirring for 30 minutes. The reaction mixture was poured into ice water. The insoluble matter so precipitated was collected by filtration, washed with water and dried under reduced pressure to give 2.06 g (93%) of isopropyl 5-[2,3-dioxo-7-fluoro-6-nitro-1,2,3,4-tetrahydroquinoxalin-1-yl]valerate.

Mass analysis (m/z): 367 (M⁺)

Nuclear magnetic resonance spectrum (DMSO-$d_6$, TMS internal standard):

δ: 1.16 (6H, d, J=6.3 Hz), 1.61–1.63 (4H, m), 2.30–2.32 (2H, m), 4.02–4.14 (2H, m), 4.88 (1H, q, J=6.3 Hz), 7.66 (1H, d, J=13.7 Hz), 7.90 (1H, d, J=7.3 Hz), 12.2 (1H, s).

5) A mixture of 1.88 g (5.11 mmol) of 5-[2,3-dioxo-7-fluoro-6-nitro-1,2,3,4-tetrahydroquinoxalin-1-yl]valerate, 765 mg of imidazole and 15 ml of DMF was stirred with heating on an oil bath of 70° C. for 10 hours under an argon gas stream. The reaction mixture was cooled to the room temperature and concentrated to half of the original volume under reduced pressure. The resulting residue was poured into ice water. The insoluble matter so precipitated was collected by filtration, washed with water and then dried under reduced pressure. To about 2.01 g of the resulting compound, 8 ml of THF and 20 ml of a 1N aqueous solution of sodium hydroxide were added under an argon gas stream, followed by stirring for 5 hours. The resulting reaction mixture was adjusted to pH 5 to 6 with an aqueous solution of hydrochloric acid. After the precipitation of the insoluble matter, the reaction mixture was heated to make it a uniform solution again, followed by filtration. The filtrate was concentrated under reduced pressure. To the resulting residue, 10 ml of water was added for recrystallization to give 1.15 g of 5-[2,3-dioxo-7-(1H-imidazol-1-yl)-6-nitro-1,2,3,4-tetrahydroquinoxalin-1-yl]valeric acid•1 hydrate•0.2 hydrate (54%).

Melting point: 236–237° C.

Elemental analysis for $C_{16}H_{15}N_5O_6 \cdot HCl \cdot 0.2H_2O$

|  | C(%) | H(%) | N(%) | Cl(%) |
|---|---|---|---|---|
| Calculated: | 46.49 | 4.00 | 16.94 | 8.56 |
| Found: | 46.34 | 3.95 | 16.88 | 8.69 |

Example 26

1) In a similar manner to Example 1-1) except for the use of 7.38 g of ethyl 6-aminohexanoate hydrochloride, 100 ml of THF, 26.3 ml of triethylamine, 35 ml of DMF and 6.00 g of 2,4-difluoronitrobenzene, 9.64 g (86%) of ethyl 6-(5-fluoro-2-nitrophenylamino)hexanoate was obtained.

Mass analysis (m/z): 298 (M⁺)

Nuclear magnetic resonance spectrum (CDCl₃, TMS internal standard):

δ: 1.10–1.97 (9H, m), 2.34 (2H, t, J=6.5 Hz), 3.10–3.42 (2H, m), 4.14 (2H, q, J=7.1 Hz), 6.22–6.62 (2H, m), 8.00–8.35 (2H, m).

2) In a similar manner to Example 1-2) except for the use of 5.00 g of ethyl 6-(5-fluoro-2-nitrophenylamino)hexanoate, 1.75 g (32%) of ethyl 6-(2,3-dioxo-7-fluoro-1,2,3,4-tetrahydroquinoxalin-1-yl)hexanoate was obtained.

Mass analysis (m/z): 323 (M⁺+1)

Nuclear magnetic resonance spectrum (DMSO-$d_6$, TMS internal standard):

δ: 0.95–1.83 (9H, m), 2.10–2.45 (2H, m), 3.86–4.28 (4H, m), 6.90–7.46 (3H, m), 11.95–12.15 (1H, br).

3) In a similar manner to Example 1–3) except for the use of 1.00 g of ethyl 6-(2,3-dioxo-7-fluoro-1,2,3,4-tetrahydroquinoxalin-1-yl)hexanoate, 1.04 g (91%) of ethyl 6-(2,3-dioxo-7-fluoro-6-nitro-1,2,3,4-tetrahydroquinoxalin-1-yl)hexanoate was obtained.

Mass analysis (m/z): 368 (M⁺+1)

Nuclear magnetic resonance spectrum (DMSO-$d_6$, TMS internal standard):

δ: 0.90–1.82 (9H, m), 2.02–2.50 (2H, m), 3.76–4.33 (4H, m), 7.66 (1H, d, J=13.7 Hz), 7.90 (1H, d, J=7.4 Hz), 12.13–12.40 (1H, br).

4) In a similar manner to Example 1–4) except for the use of 392 mg of ethyl 6-(2,3-dioxo-7-fluoro-6-nitro-1,2,3,4-tetrahydroquinoxalin-1-yl)hexanoate, 160 mg of imidazole and 2.5 ml of DMF, 318 mg (74%) of 6-[2,3-dioxo-7-(1H-imidazol-1-yl)- 6-nitro-1,2,3,4-tetrahydroquinoxalin-1-yl]hexanoate•0.9 hydrate was obtained.

Melting point: 120–123° C.

Elemental analysis for $C_{17}H_{17}N_5O_6 \cdot 0.9\,H_2O$

|  | C(%) | H(%) | N(%) |
|---|---|---|---|
| Calculated: | 50.60 | 4.70 | 17.35 |
| Found: | 50.63 | 4.38 | 17.32 |

Mass analysis (m/z): 388 (M⁺+1)

Nuclear magnetic resonance spectrum (DMSO-$d_6$, TMS internal standard):

δ: 1.20–1.32 (2H, m), 1.48–1.59 (2H, m), 1.77–1.89 (2H, m), 2.19 (2H, t, J=7.3 Hz), 4.34 (2H, t, J=7.3 Hz), 7.09 (1H, s), 7.43 (1H, s), 7.90 (1H, s), 8.11 (1H, s), 8.51 (1H, s), 8.66 (1H, s), 11.97 (1H, s).

Example 27

To a mixture of 0.19 ml of a 30% aqueous solution of hydrogen peroxide and 1.2 ml of a 1N aqueous solution of sodium hydroxide, 150 mg of 2-[6-cyano-2,3-dioxo-7-(1H-imidazol-1-yl-1,2,3,4-tetrahydroquinoxalin-1-yl)acetic acid was added, followed by stirring at room temperature for 30 minutes. The reaction mixture was adjusted to about pH 1 with 1N hydrochloric acid. The crystals so precipitated were collected by filtration, washed with water and dried under reduced pressure to give 138 mg (81%) of 2-[6-carbamoyl-2,3-dioxo-7-(1H-imidazol-1-yl-1,2,3,4-tetrahydroquinoxalin-1-yl)acetic acid•1.4 hydrate.

Melting point: >300° C.

Elemental analysis for $C_{14}H_{11}N_5O_5 \cdot 1.4 H_2O$

|  | C (%) | H (%) | N (%) |
|---|---|---|---|
| Calculated: | 47.44 | 3.92 | 19.76 |
| Found: | 47.36 | 3.82 | 19.88 |

Mass analysis (m/z): 330 ($M^+$+1)

Nuclear magnetic resonance spectrum (DMSO-$d_6$, TMS internal standard):

δ: 4.94 (2H, s), 7.04 (1H, s), 7.26–7.34 (2H, m), 7.45 (1H, s), 7.51 (1H, s), 7.72–7.80 (2H, m), 12.39 (1H, s).

Example 28

1) In 16.ml of concentrated sulfuric acid, 3.29 g (11.8 mmol) of ethyl 4-(2,4-difluorophenoxy)benzoate was dissolved at the temperature not higher than 5° C. To the resulting mixture, 520 pl of fuming nitric acid was added at −5° C. or lower under stirring, followed by stirring for 30 minutes at the same temperature. The reaction mixture was poured into ice water and the insoluble matter so precipitated was collected by filtration. The resulting compound was dissolved in chloroform. The resulting solution was washed successively with water and brine, dried over anhydrous sodium sulfate and then concentrated under reduced pressure. The resulting residue was purified by chromatography on a silica gel column (developing solvent: hexane:ethyl acetate=8:1) to give 2.42 g (63%) of ethyl 4-(2,4-difluoro-5-nitrophenoxy)benzoate.

Nuclear magnetic resonance spectrum (CDCl$_3$, TMS internal standard):

δ: 1.40 (3H, t, J=7.3 Hz), 4.38 (2H, q, J=7.3 Hz), 7.02 (2H, d, J=9.2 Hz), 7.21 (1H, t(dd), J=9.8 Hz), 7.91 (1H, t(dd), J=7.6 Hz), 8.08 (2H, d, J=9.2 Hz).

Mass analysis (m/z): 323 ($M^+$)

2) A mixture of 2.38 g (7.36 mmol) of ethyl 4-(2,4-difluoro-5-nitrophenoxy)benzoate, 1.03 g of glycine ethyl ester hydrochloride, 30 ml of THF, 10 ml of DMF and 2.06 ml of triethylamine was subjected to heating under reflux for 10 hours. After cooling, the reaction mixture was diluted with ethyl acetate. The insoluble matter was removed by filtration and the filtrate was concentrated under reduced pressure. The resulting residue was dissolved in ethyl acetate. The resulting solution was washed successively with water and brine, dried over anhydrous sodium sulfate and then, concentrated under reduced pressure. The resulting residue was purified by chromatography on a silica gel column (developing solvent: hexane:dichloromethane:ethyl acetate=8:2:1) to give 1.81 g (61%) of N-[4-(4-ethoxycarbonylphenoxy)-5-fluoro-2-nitrophenyl]glycine ethyl ester.

Mass analysis (m/z): 406 ($M^+$)

Nuclear magnetic resonance spectrum (CDCl$_3$, TMS internal standard):

δ: 1.34 (3H, t, J=7.3 Hz), 1.38 (3H, t, J=7.0 Hz), 4.09 (2H, d, J=2.9 Hz), 4.32 (2H, q, J=7.3 Hz), 4.36 (2H, q, J=7.0 Hz), 6.52 (2H, d, J=12.2 Hz), 6.95 (2H, d, J=9.1 Hz), 8.03 (2H, d, J=9.1 Hz), 8.11 (1H, d, J=11.6 Hz), 8.51 (1H, bs).

3) A mixture of 1.78 g (4.39 mmol) of N-[4-(4-ethoxycarbonylphenoxy)-5-fluoro-2-nitrophenyl]glycine ethyl ester, 896 mg of imidazole and 20 ml of DMF was stirred with heating on an oil bath of 70° C. for 12 hours. After cooling, the reaction mixture was concentrated under reduced pressure. The resulting residue was dissolved in ethyl acetate. The resulting solution was washed successively with water and brine, dried over anhydrous sodium sulfate and then, concentrated under reduced pressure. The resulting residue was purified by chromatography on a silica gel column (developing solvent: chloroform+0 to 1% methanol) to give 1.49 g (75%) of N-[4-(4-ethoxycarbonylphenoxy)-5-(1H-imidazol-1-yl)-2-nitrophenyl]glycine ethyl ester.

Mass analysis (m/z): 454 ($M^+$)

Nuclear magnetic resonance spectrum (DMSO-$d_6$, TMS internal standard):

δ: 1.34 (3H, t, J=7.3 Hz), 1.37 (3H, t, J=7.2 Hz), 4.14 (2H, d, J=4.9 Hz), 4.31 (2H, q, J=7.3 Hz), 4.33 (2H, q, J=7.2 Hz), 6.74 (1H, s), 6.88 (2H, d, J=9.2 Hz), 7.10 (1H, s), 7.22 (1H, s), 7.83 (1H, s), 7.95 (2H, d, J=9.2 Hz), 8.11 (1H, s), 8.46–9.48 (1H, m).

4) A mixture of 1.46 g (3.19 mmol) of N-[4-(4-ethoxycarbonylphenoxy)-5-(1H-imidazol-1-yl)-2-nitrophenyl]glycine ethyl ester, 100 ml of THF and 410 mg of 10% palladium-carbon was stirred at room temperature and normal pressure under a hydrogen gas atmosphere for 6 hours. After the reaction, the catalyst was removed by filtration. To the filtrate, 2.02 ml of triethylamine was added, followed by ice-cooling under an argon gas stream. To the reaction mixture, a mixture of 1.37 ml of ethyl chloroglyoxylate and 15 ml of THF was added dropwise under stirring. The reaction mixture was stirred further for 2 hours. The insoluble matter was then removed by filtration and the filtrate was concentrated under reduced pressure. Then, 100 ml of ethanol was added to the resulting residue, followed by heating under reflux for 18 hours. After cooling, the reaction mixture was concentrated under reduced pressure. The resulting residue was purified by chromatography on a silica gel column (developing solvent: chloroform+5 to 10% methanol) to give 1.19 g (78%) of ethyl 2-[2,3-dioxo-6-(4-ethoxycarbonylphenoxy)-7-(1H-imidazol-1-yl)-1,2,3,4-tetrahydroquinoxalin-1-yl]acetate.

Mass analysis (m/z): 478 ($M^+$)

Nuclear magnetic resonance spectrum (CDCl$_3$, TMS internal standard):

δ: 1.22 (3H, t, J=7.0 Hz), 1.30 (3H, t, J=7.0 Hz), 4.18 (2H, q, J=7.0 Hz), 4.28 (2H, q, J=7.0 Hz), 5.04 (2H, s), 6.98 (1H, s), 7.04–7.08 (3H, m), 7.41 (1H, s), 7.71 (1H, s), 7.88 (1H, s), 7.90–7.93 (3H, m), 12.24 (1H, s).

Example 29

1) In 20 ml of DMF, 500 mg of 7-fluoro-1-hydroxy-6-nitro-2,3(1H,4H)-quinoxalinedione was dissolved. To the aresulting solution, 83 mg of sodium hydride was added, followed by stirring for 10 minutes. To the reaction -z mixture, 218 ml of ethyl bromoacetate was added, followed by reaction for 2 days. The reaction mixture was poured into a saturated aqueous solution of ammonium chloride, followed by extraction with chloroform three times. The organic layer was concentrated, followed by recrystallization from 2-propanol to give 481 mg of ethyl 2-[(2,3-dioxo-7-fluoro-6-nitro-1,2,3,4-tetrahydroquinoxalinyl)oxy]acetate.

Mass analysis (m/z): 328 ($M^+$+1)

Nuclear magnetic resonance spectrum (DMSO-$d_6$, TMS internal standard):

δ: 1.23 (3H, t, J=7.2 Hz), 4.19 (2H, q, J=7.2 Hz), 4.96 (2H, s), 7.73 (1H, d, J=12.4 Hz), 7.91 (1H, d, J=6.8 Hz).

2) In a similar manner to Example 4–4) except for the use of ethyl 2-[(2,3-dioxo-7-fluoro-6-nitro-1,2,3,4-tetrahydroquinoxalinyl)oxy]acetate, ethyl 2-[(2,3-dioxo-7-(1H-imidazol-1-yl)-6-nitro-1,2,3,4-tetrahydroquinoxalinyl)oxy]acetate was obtained.

Mass analysis (m/z): 376 (M$^+$+1)

Nuclear magnetic resonance spectrum (DMSO-d$_6$, TMS internal standard):

δ: 1.16 (3H, t, J=5.2 Hz), 4.16 (2H, q, J=5.2 Hz), 4.97 (2H, s), 7.05 (1H, s), 7.11 (1H, s), 7.45 (1H, s), 7.78 (1H, s), 7.95 (1H, s).

3) In a similar manner to Example 4–5) except for the use of ethyl 2-[(2,3-dioxo-7-fluoro-6-nitro-1,2,3,4-tetrahydroquinoxalinyl)oxy]acetate, 2-[(2,3-dioxo-7-(1H-imidazol-1-yl)-6-nitro-1,2,3,4-tetrahydroquinoxalinyl)oxy]acetic acid.2 hydrate was obtained.

Melting point: >300° C.

Nuclear magnetic resonance spectrum (DMSO-d$_6$, TMS internal standard):

δ: 4.41 (2H, s), 7.08 (1H, s), 7.40 (1H, s), 7.88 (1H, s), 7.92 (1H, s), 8.30 (1H, s).

Example 30

1) In a similar manner to Example 1–1) except for the use of 2,6-dichloro-3-nitropyridine and glycine ethyl ester hydrochloride, N-(6-chloro-3-nitropyridin-2-yl)glycine ethyl ester was obtained.

Mass analysis (m/z): 260 (M$^+$+1)

Nuclear magnetic resonance spectrum (CDCl$_3$, TMS internal standard):

δ: 1.32 (3H, d, J=7.2 Hz), 4.28 (2H, q, J=7.2 Hz), 4.36 (2H, d, J=5.2 Hz), 6.70 (1H, d, J=8.0 Hz), 8.38 (1H, d, J=8.0 Hz).

2) In a similar manner to Example 28–3) except for the use of N-(6-chloro-3-nitropyridin-2-yl)glycine ethyl ester, N-(6-(1H-imidazol-1-yl)-3-nitropyridin-2-yl)glycine ethyl ester was obtained.

Mass analysis (m/z): 292 (M$^+$+1)

Nuclear magnetic resonance spectrum (DMSO-d$_6$, TMS internal standard):

δ: 1.18 (3H, d, J=7.2 Hz), 4.14 (2H, q, J=7.2 Hz), 4.32 (2H, d, J=5.2 Hz), 7.17 (1H, s), 7.23 (1H, d, J=9.2 Hz), 7.94 (1H, s), 8.58 (1H, s), 8.64 (1H, d, J=9.2 Hz).

3) In a similar manner to Example 1–2) except for the use of N-(6-(1H-imidazol-1-yl)-3-nitropyridin-2-yl)glycine ethyl ester, ethyl 2-(2,3-dioxo-6-(1H-imidazol-1-yl)-1,2,3,4-tetrahydropyrido[2,3-b]pyrazin-4-yl)acetate was obtained.

Mass analysis (m/z): 316 (M$^+$+1)

Nuclear magnetic resonance spectrum (DMSO-d$_6$, TMS internal standard):

δ: 1.19 (3H, d, J=6.0 Hz), 4.16 (2H, q, J=6.0 Hz), 5.06 (2H, s), 7.14 (1H, s), 7.64 (1H, d, J=6.8 Hz), 7.70 (1H, d, J=6.0 Hz), 7.92 (1H, s), 8.53 (1H, s).

4) In 30 ml of acetonitrile, 730 mg. of ethyl 2-(2,3-dioxo-6-(1H-imidazol-1-yl)-1,2,3,4-tetrahydropyrido[2,3-b]pyrazin-4-yl)acetate was dissolved. While cooling on an ice bath, 615 mg of nitronium tetrafluoroborate was added. After stirring on an ice bath for 2 hours, the reaction mixture was concentrated. To the concentrate, a 1N aqueous solution of potassium hydroxide was added, followed by stirring for 2 hours. The reaction mixture was neutralized with 1N hydrochloric acid, followed by purification by chromatography on a C18 column to give 364 mg of ammonium 2-(2,3-dioxo-6-(1H-imidazol-1-yl)-7-nitro-1,2,3,4-tetrahydropyrido[2,3-b]pyrazin-4-yl)acetate•1 hydrate.

Melting point: 241–245° C.

Nuclear magnetic resonance spectrum (DMSO-d$_6$, TMS internal standard):

δ: 4.58 (2H, s), 7.05 (1H, s), 7.45 (1H, s), 7.99 (1H, s), 8.12 (1H, s).

Example 31

In a similar manner to Example 1 except for the use of 2,4-difluoronitrobenzene and alanine ethyl ester hydrochloride, 2-(2,3-dioxo-7-(1H-imidazol-1-yl)-6-nitro-1,2,3,4-tetrahydroquinoxalinyl)propionic acid•1 hydrochloride•1 hydrate was obtained.

Melting point: 129–133° C.

Nuclear magnetic resonance spectrum (DMSO-d$_6$, TMS internal standard):

δ: 2.50 (2H, d, J=5.6 Hz), 4.24 (1H, q, J=5.6 Hz), 6.89 (1H, s), 7.79 (1H, s), 7.88 (1H, s), 7.99 (1H, s), 8.36 (1H, s).

Example 32

In a similar manner to Example 1 except for the use of 2,4-difluoronitrobenzene and phenylalanine ethyl ester hydrochloride, ethyl 2-(2,3-dioxo-7-(1H-imidazol-1-yl)-6-nitro-1,2,3,4-tetrahydroquinoxalinyl)-3-(4-nitrophenyl)propionate was obtained.

Mass analysis (m/z): 495 (M$^+$+1)

Nuclear magnetic resonance spectrum (DMSO-d$_6$, TMS internal standard):

δ: 0.90–1.30 (3H, br), 3.15–3.12 (2H, br), 4.10–4.40 (1H, br), 4.58 (1H, br), 6.52-(1H, d, J=10.8 Hz), 7.36 (1H, d, J=6.0 Hz), 7.48 (2H, d, J=8.0 Hz), 7.71 (1H, s), 7.83 (1H, s), 7.96 (1H, s), 8.13 (2H, d, J=6.8 Hz).

Example 33

The final by-product of Example 24–2) was recrystallized from a 1N aqueous solution of hydrochloric acid to give 2-[2,3-dioxo-7-(1H-imidazol-1-yl)-5-nitro-1,2,3,4-tetrahydroquinoxalin-1-yl]acetic acid•0.5 HCl•0.5 hydrate.

Melting point: 268° C. (decomposition) (1N HCl)

Elemental analysis for $C_{13}H_9N_5O_6 \cdot 0.5\ HCl \cdot 0.5\ H_2O$

|  | C (%) | H (%) | N (%) | Cl (%) |
|---|---|---|---|---|
| Calculated: | 43.56 | 2.95 | 19.54 | 4.94 |
| Found: | 43.81 | 2.88 | 19.57 | 5.17 |

Mass analysis (m/z): 332 (M$^+$+1)

Nuclear magnetic resonance spectrum (DMSO-d$_6$, TMS internal standard):

δ: 5.06 (2H, s), 7.58 (1H, s), 8.06 (1H, s), 8.20 (1H, s), 8.35 (1H, s), 9.19 (1H, s).

Hereinafter, the chemical structural formula of each of the compounds obtained in Examples will be shown in the following tables.

TABLE 2

| Example | Chemical structural formula |
|---|---|
| 1 and 23 and 24 | imidazolyl-quinoxaline-2,3-dione with NO$_2$ and N-CH$_2$COOH |
| 2 | imidazolyl-quinoxaline-2,3-dione with NO$_2$ and N-(CH$_2$)$_2$COOH |
| 3 | imidazolyl-quinoxaline-2,3-dione with NO$_2$ and N-(CH$_2$)$_3$COOH |
| 4 | imidazolyl-quinoxaline-2,3-dione with O$_2$N (upper) and N-CH$_2$COOH |
| 5 | imidazolyl-quinoxaline-2,3-dione with H$_2$N and N-CH$_2$COOH |

TABLE 3

| Example | Chemical structural formula |
|---|---|
| 6 | imidazolyl-quinoxaline-2,3-dione with O$_2$N and N-CH$_2$CONH$_2$ |
| 7 | imidazolyl-quinoxaline-2,3-dione with CH$_3$HN and N-CH$_2$COOH |

TABLE 3-continued

| Example | Chemical structural formula |
|---|---|
| 8 | imidazolyl-quinoxaline-2,3-dione with (CH$_3$)$_2$N and N-CH$_2$COOH |
| 9 | imidazolyl-quinoxaline-2,3-dione with F$_3$C and N-CH$_2$COOH |
| 10 | imidazolyl-quinoxaline-2,3-dione with CH$_3$O and N-CH$_2$COOH |

TABLE 4

| Example | Chemical structural formula |
|---|---|
| 11 | imidazolyl-quinoxaline-2,3-dione with HOOCCH$_2$O and N-CH$_2$COOH |
| 12 | imidazolyl-quinoxaline-2,3-dione with HOOC and N-CH$_2$COOH |
| 13 | imidazolyl-quinoxaline-2,3-dione with NC and N-CH$_2$COOH |
| 14 | imidazolyl-quinoxaline-2,3-dione with CH$_3$ and N-CH$_2$COOH |

TABLE 4-continued
| Example | Chemical structural formula |
|---|---|
| 15 | 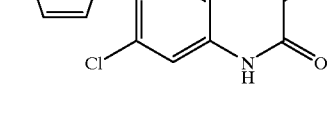 |
TABLE 5
| Example | Chemical structural formula |
|---|---|
| 16 | 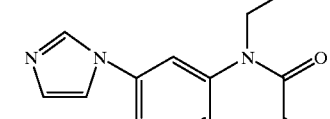 |
| 17 | |
| 18 | |
| 19 | |
| 20 | |
TABLE 6
| Example | Chemical structural formula |
|---|---|
| 21 |  |
| 22 | |
| 25 | |
| 26 | |
| 27 | |
TABLE 7
| Example | Chemical structural formula |
|---|---|
| 28 | 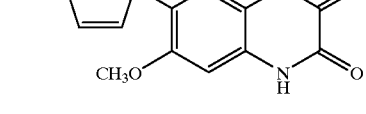 |

TABLE 7-continued

| Example | Chemical structural formula |
|---|---|
| 29 | (imidazolyl-quinoxaline structure with O-CH2-COOH, NO2) |
| 30 | (imidazolyl-pyrido-pyrazine structure with CH2-COOH, NO2) |
| 31 | (imidazolyl-quinoxaline with CH(CH3)-COOH, NO2) |
| 32 | (imidazolyl-quinoxaline with CH(COOC2H5)-CH2-C6H4-NO2, NO2) |
| 33 | (imidazolyl-quinoxaline with CH2-COOH, NO2) |

Each of the compounds which will be shown below can be prepared in the substantially same manner to the processes described in the above-described preparation process or those described in Examples, or by applying a slightly modified processes thereof apparent to those skilled in the art.

1) 2[2,3-dioxo-7-(4-carboxyphenoxy)-6-(1H-imidazol-1-yl)-1,2,3,4-tetrahydroquinoxalin-1-yl]acetic acid
2) 2[2,3-dioxo-7-(4-carboxybenzyloxy)-6-(1H-imidazol-1-yl)-1,2,3,4-tetrahydroquinoxalin-1-yl]acetic acid
3) 5-[2,3-dioxo-7-(1H-imidazol-1-yl)-6-nitro-1,2,3,4-tetrahydroquinoxalin-1-yl]-2,2-dimethylpentanoic acid
4) Ethyl 5-[2,3-dioxo-7-(1H-imidazol-1-yl)-6-nitro-1,2,3,4-tetrahydroquinoxalin-1-yl]valerate
5) 5-[2,3-dioxo-7-(1H-imidazol-1-yl)-6-nitro-1,2,3,4-tetrahydroquinoxalin-1-yl]pentanamide
6) 5-[2,3-dioxo-7-(1H-imidazol-1-yl)-6-nitro-1,2,3,4-tetrahydroquinoxalin-1-yl]-2,4-dimethylpentanoic acid
7) 5-[2,3-dioxo-7-(1H-imidazol-1-yl)-6-nitro-1,2,3,4-tetrahydroquinoxalin-1-yl]-4-phenylpentanoic acid
8) 4-[(2,3-dioxo-7-(1H-imidazol-1-yl)-6-nitro-1,2,3,4-tetrahydroquinoxalinyl)oxy]butyric acid Formulation Example A formulation example of the invention compound as a pharmaceutical preparation is shown below.

A lyophilized preparation
in one vial

TABLE 8

| Compound of Example 1 | 50 mg (0.5%) |
|---|---|
| Citric acid | 210 mg (2.1%) |
| D-mannitol | 100 mg (1.0%) |
| | 10 ml |

In 800 ml of water, 5 g of the compound of Example 1, 21 g of citric acid and 10 g of D-mannitol were added successively to dissolve the latter in the former. Water was added to make the total amount of 1000 ml.

After sterile filtration, a 10 ml portion of the solution was filled in a brown vial, followed by lyophilization to obtain a dissolution-upon-use type injection.

What is claimed is:

1. 2-[2,3-Dioxo-7-(1H-imidazol-1-yl)-6-nitro-1,2,3,4-tetrahydroquinoxalin-1-yl]acetic acid or salt thereof.

2. 2-[6-Benzyloxy-2,3-dioxo-7-(1H-imidazol-1-yl)-1,2,3,4-tetrahydroquinoxalin-1-yl]acetic acid or salt thereof.

3. A composition for inhibiting AMPA receptor, for achieving anti-ischemic activity or for achieving psychotropic activity comprising a therapeutically effective amount of a compound as claimed in claim 1.

* * * * *